United States Patent
Hensler et al.

(10) Patent No.: US 9,833,246 B2
(45) Date of Patent: Dec. 5, 2017

(54) COLLECTING AND HARVESTING CUT BONE FROM KERRISON RONGEUR

(71) Applicant: H & M INNOVATIONS, LLC, Wilmington, NC (US)

(72) Inventors: Robert Sean Hensler, Wilmington, NC (US); Thomas Eric Melin, Wilmington, NC (US); Ryan Shane Gorman, Charlotte, NC (US); Raeshon Lamont McNeil, Charlotte, NC (US); Michael Morgan Starkey, Charlotte, NC (US); Thomas James Philpott, Charlotte, NC (US)

(73) Assignee: H & M INNOVATIONS, LLC, Wilmington, NC (US)

( * ) Notice: Subject to any disclaimer, the term of this patent is extended or adjusted under 35 U.S.C. 154(b) by 0 days.

(21) Appl. No.: 14/679,903

(22) Filed: Apr. 6, 2015

(65) Prior Publication Data

US 2015/0282816 A1    Oct. 8, 2015

Related U.S. Application Data

(63) Continuation of application No. PCT/US2015/024402, filed on Apr. 4, 2015.
(Continued)

(51) Int. Cl.
*A61M 1/00* (2006.01)
*A61B 17/16* (2006.01)
(Continued)

(52) U.S. Cl.
CPC .......... *A61B 17/1604* (2013.01); *A61B 17/16* (2013.01); *A46B 9/00* (2013.01);
(Continued)

(58) Field of Classification Search
CPC ..... A61B 17/1604; A61B 90/70; A61B 17/16; A61B 17/1608; A61B 2017/00969; A61B 2217/002; A46B 9/00; A46B 57/60
(Continued)

(56) References Cited

U.S. PATENT DOCUMENTS 2,121,307 A * 6/1938 Swift ........................ 15/104.001
4,087,878 A * 5/1978 Grieshaber et al. ... A61B 90/70
15/104.92
(Continued)

FOREIGN PATENT DOCUMENTS

WO    2015154060 A3    10/2015

OTHER PUBLICATIONS

International Search Report and Written Opinion in PCT/US2015/024402 by the USPTO, dated Sep. 30, 2015, 11 pages.

*Primary Examiner* — Tatyana Zalukaeva
*Assistant Examiner* — Andrew J Mensh
(74) *Attorney, Agent, or Firm* — Tillman Wright, PLLC; Chad D. Tillman

(57) ABSTRACT

A collector used to collect bone includes: a container body defining an interior containment space for receiving and retaining collected bone, and having at least one open end for access and removal of collected bone from the interior containment space; and a cap in covering relation to the open end of the container body such that access to the interior containment space for removal of collected bone is inhibited. The collector includes an intake port defining an opening for receiving therein a distal end of a kerrison rongeur for collecting cut bone from a cutting area thereof, and the cap includes at least one scraper for engaging and dislodging cut bone from the cutting area of a distal end of a kerrison rongeur when received within the intake port. The
(Continued)

collector preferably is used with a kerrison-type rongeur for collecting cut bone therefrom.

18 Claims, 34 Drawing Sheets

Related U.S. Application Data

(60) Provisional application No. 61/975,698, filed on Apr. 4, 2014.

(51) Int. Cl.
   *A63B 47/04* (2006.01)
   *B08B 1/00* (2006.01)
   *A61B 90/70* (2016.01)
   *A63B 57/60* (2015.01)
   *A46B 9/00* (2006.01)
   *A61B 17/00* (2006.01)
   *A61F 2/46* (2006.01)

(52) U.S. Cl.
   CPC .......... *A61B 17/1608* (2013.01); *A61B 90/70* (2016.02); *A61B 2017/00969* (2013.01); *A61B 2217/002* (2013.01); *A61F 2/4644* (2013.01); *A63B 57/60* (2015.10)

(58) Field of Classification Search
   USPC .............................. 604/317; 15/21.1, 104.92
   See application file for complete search history.

(56) References Cited

U.S. PATENT DOCUMENTS

| | | | | |
|---|---|---|---|---|
| 4,872,235 | A | * | 10/1989 | Nielsen .................. A45D 24/44 15/104.92 |
| 5,298,077 | A | * | 3/1994 | Saarela .................. A46B 15/00 134/6 |
| 6,964,078 | B2 | * | 11/2005 | Schwab ................. A61B 90/70 15/218.1 |
| 2001/0005786 | A1 | | 6/2001 | Michelson |
| 2002/0069472 | A1 | * | 6/2002 | Glass .................... A63B 57/60 15/104.92 |
| 2005/0027265 | A1 | * | 2/2005 | Maki et al. ...... A61B 17/32037 604/267 |
| 2011/0202063 | A1 | | 8/2011 | Bonnin |
| 2013/0345596 | A1 | | 12/2013 | Zimmon |
| 2014/0074240 | A1 | | 3/2014 | Hensler |
| 2014/0209119 | A1 | | 7/2014 | Fleming |

\* cited by examiner prior art Kerrison rongeur

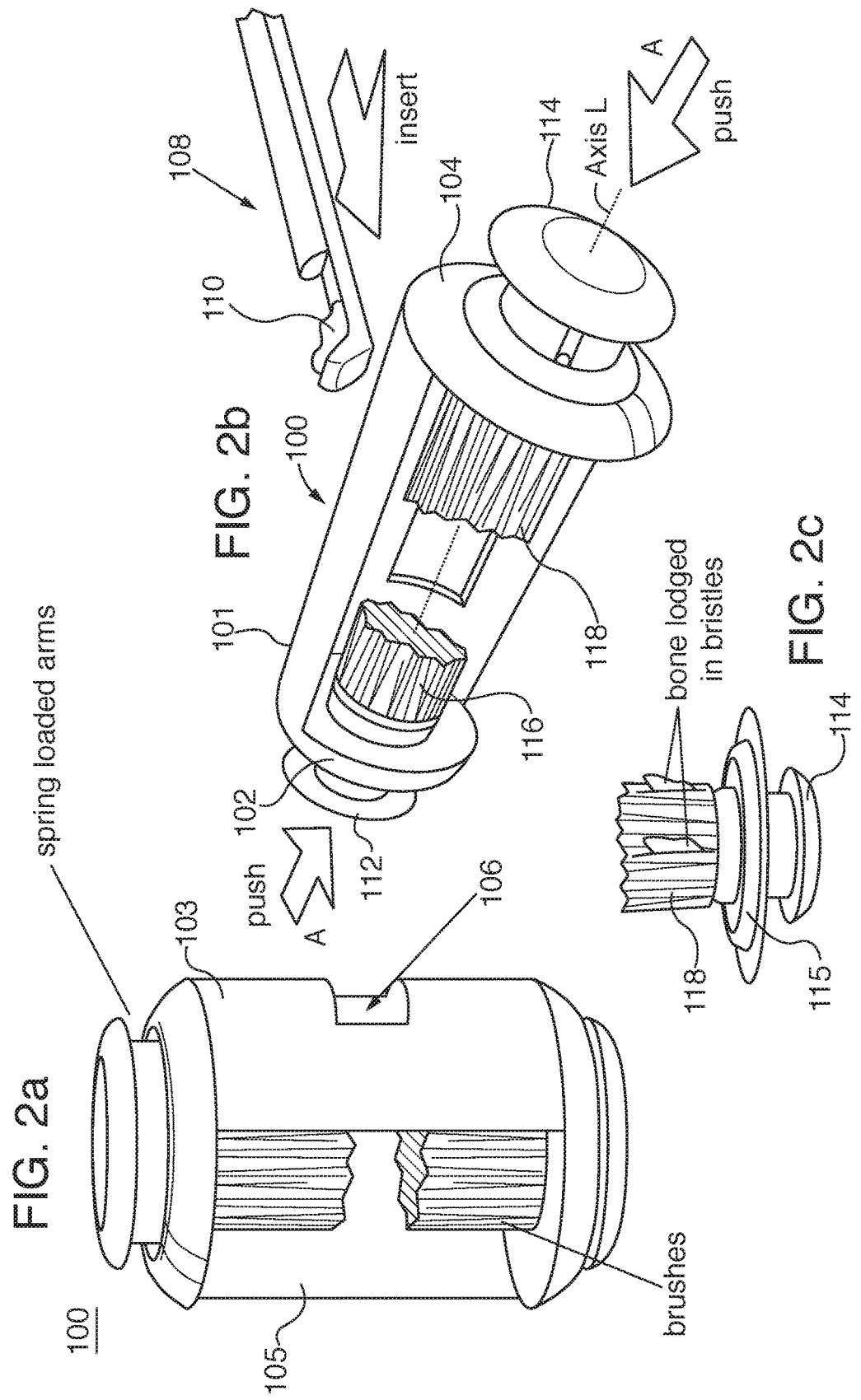

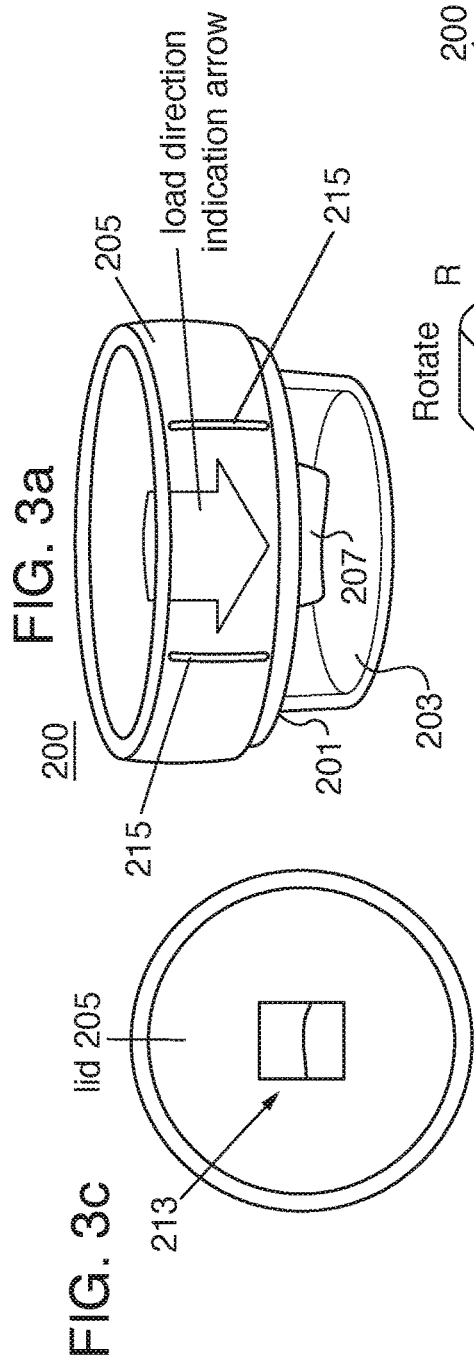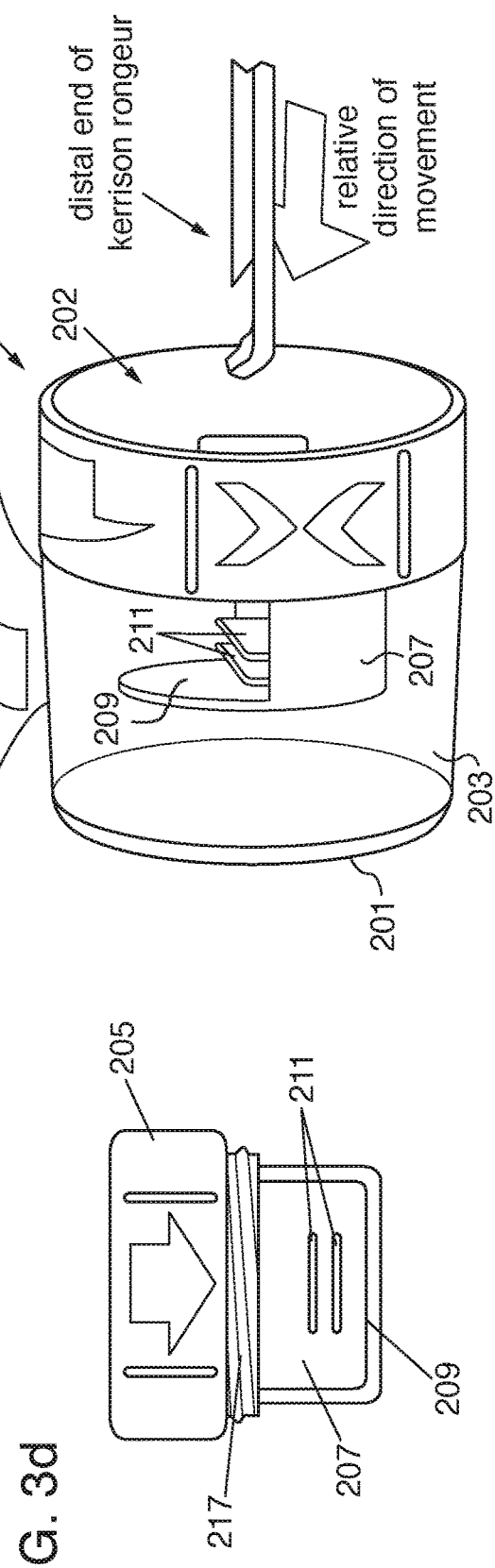

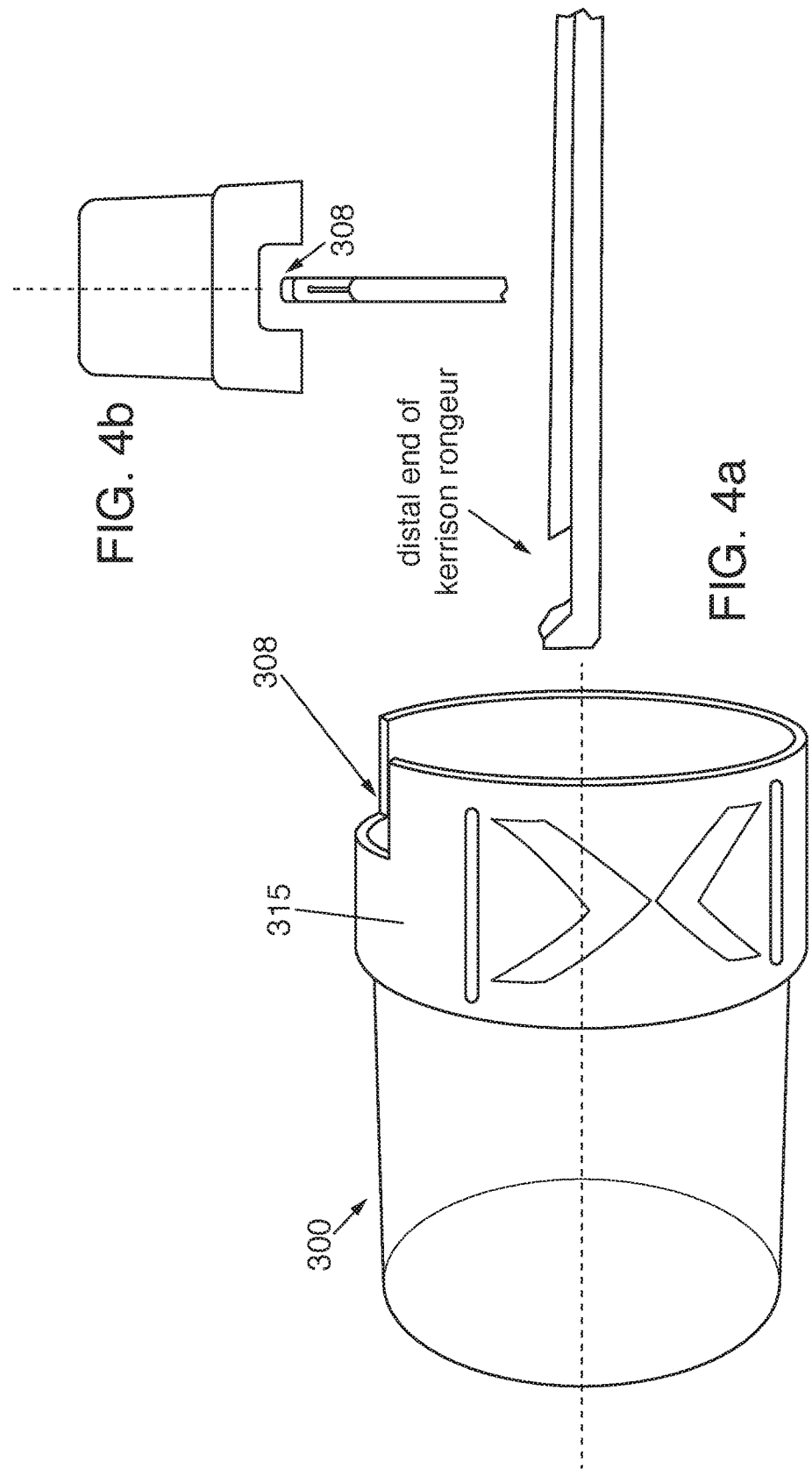

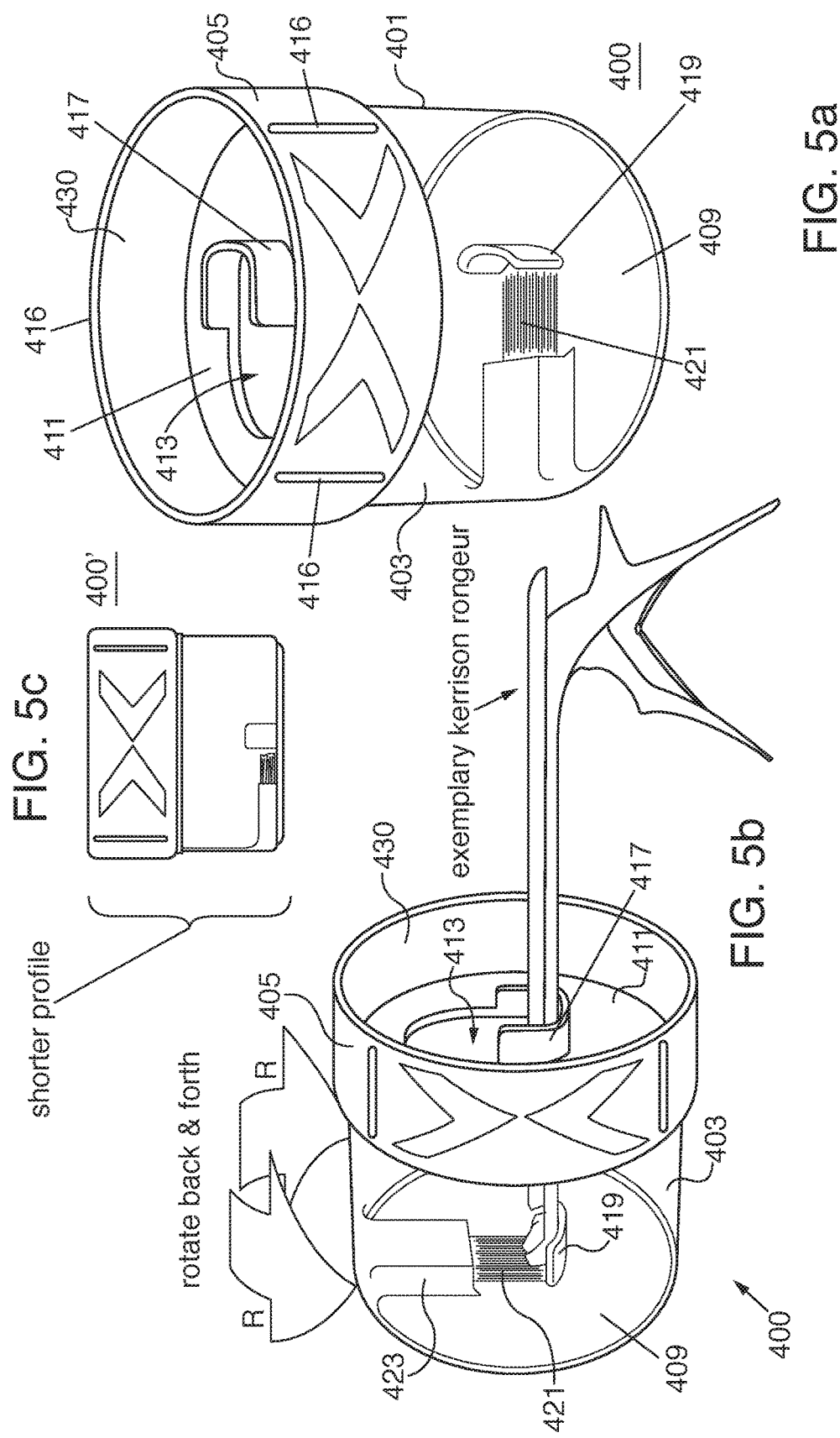

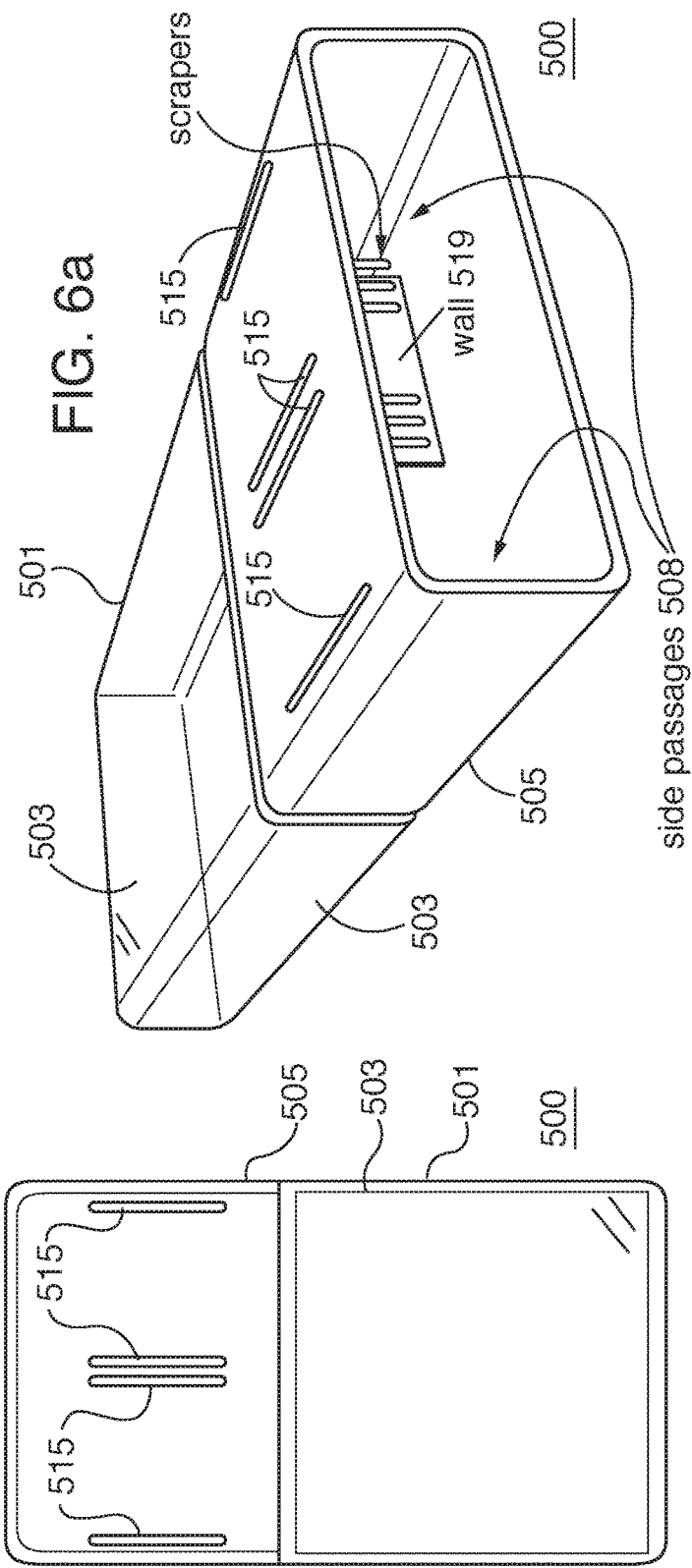

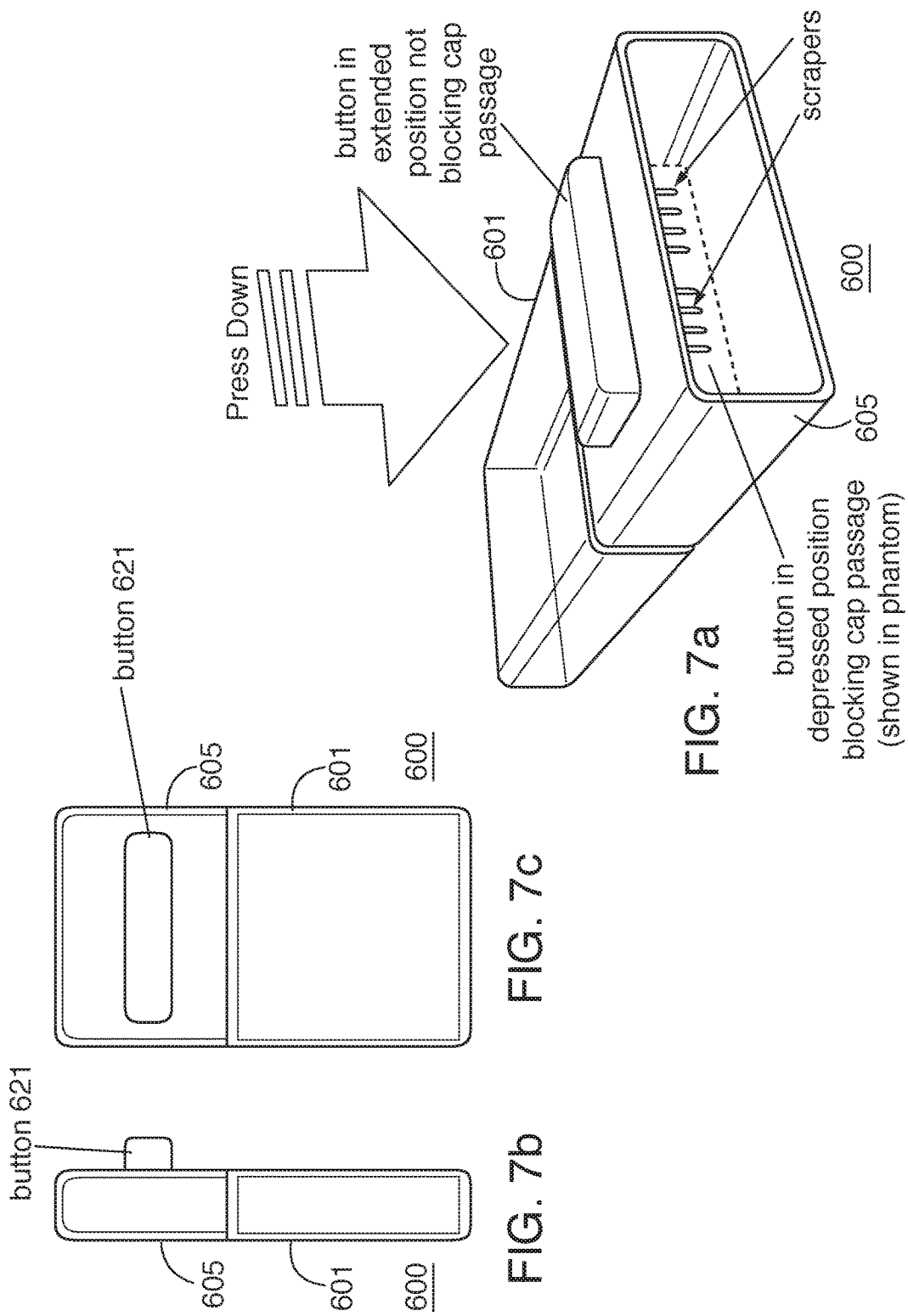

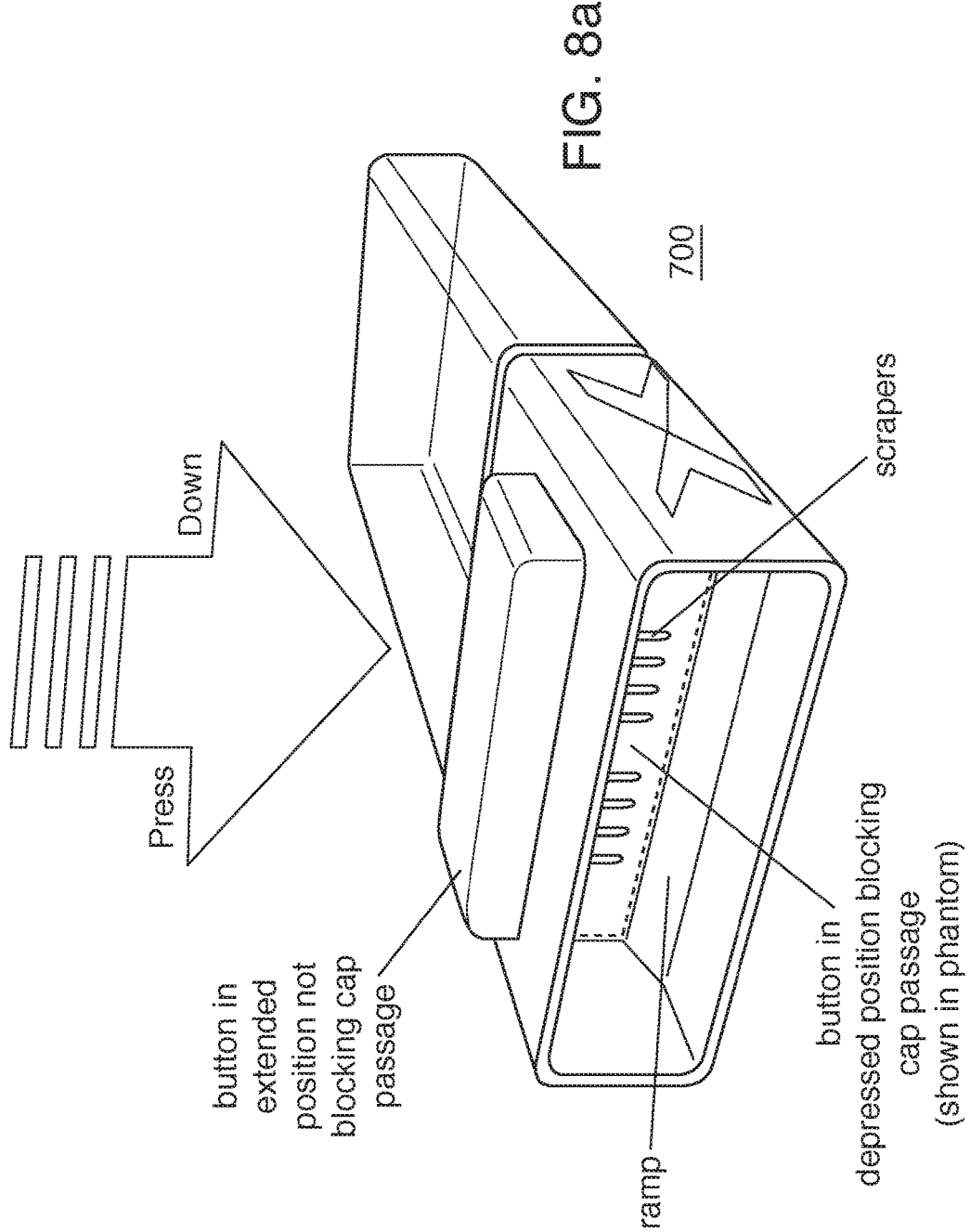

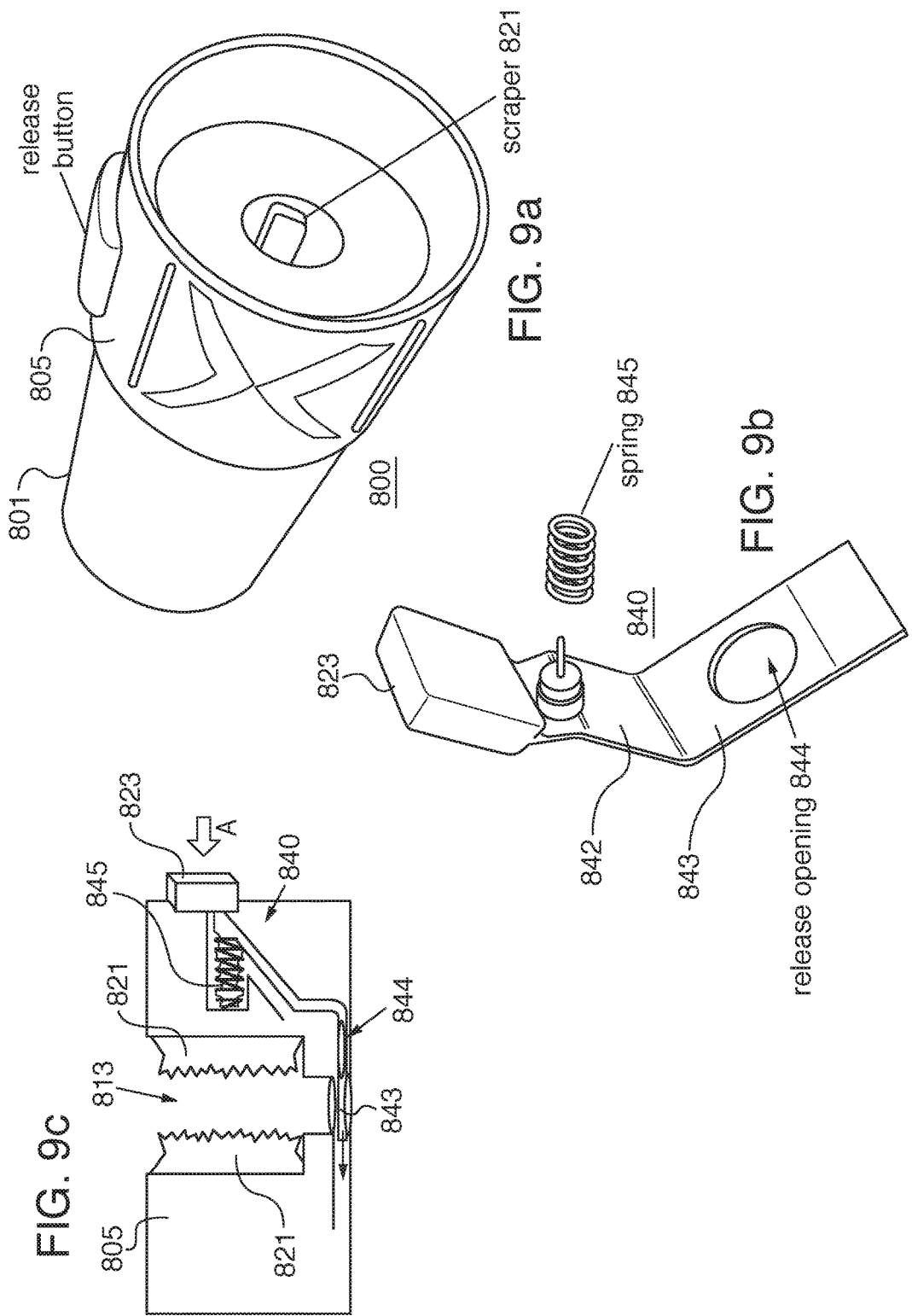

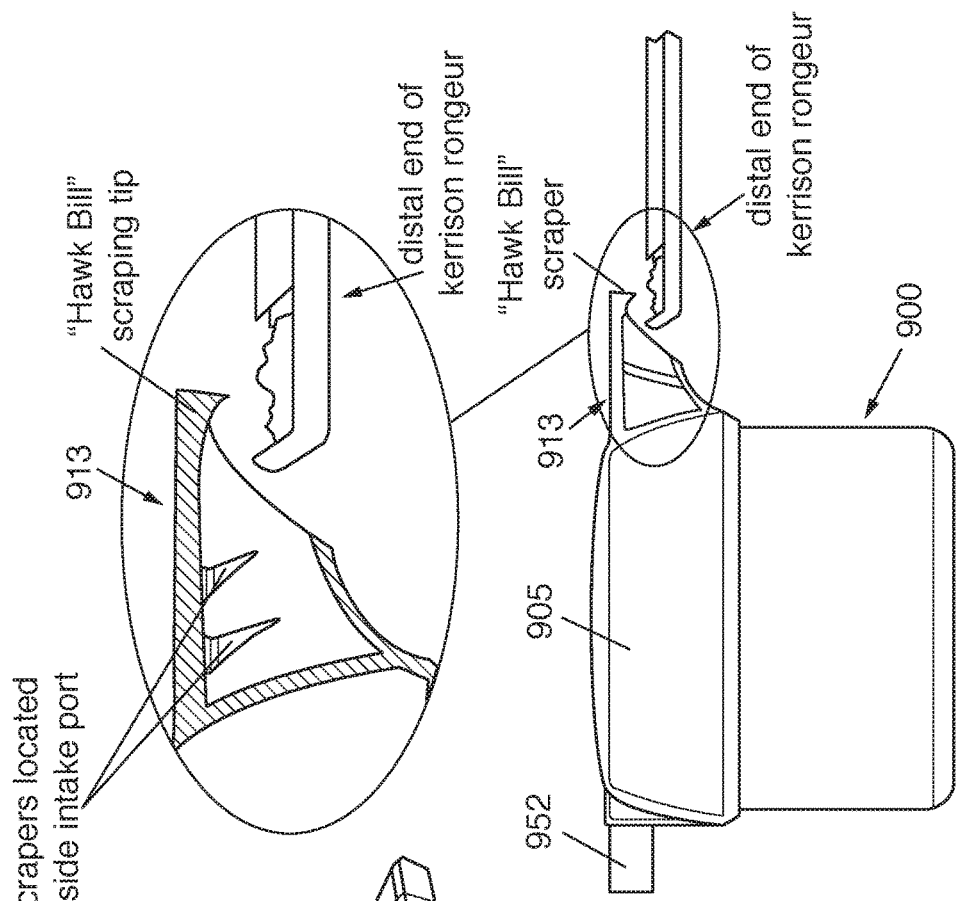
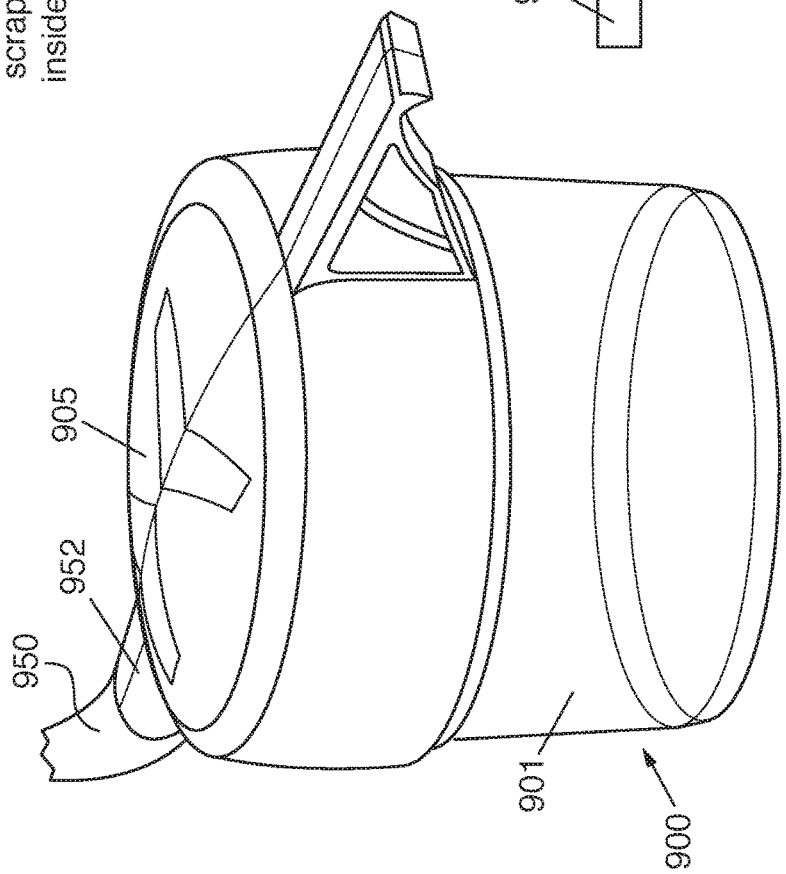
FIG. 10a
FIG. 10b

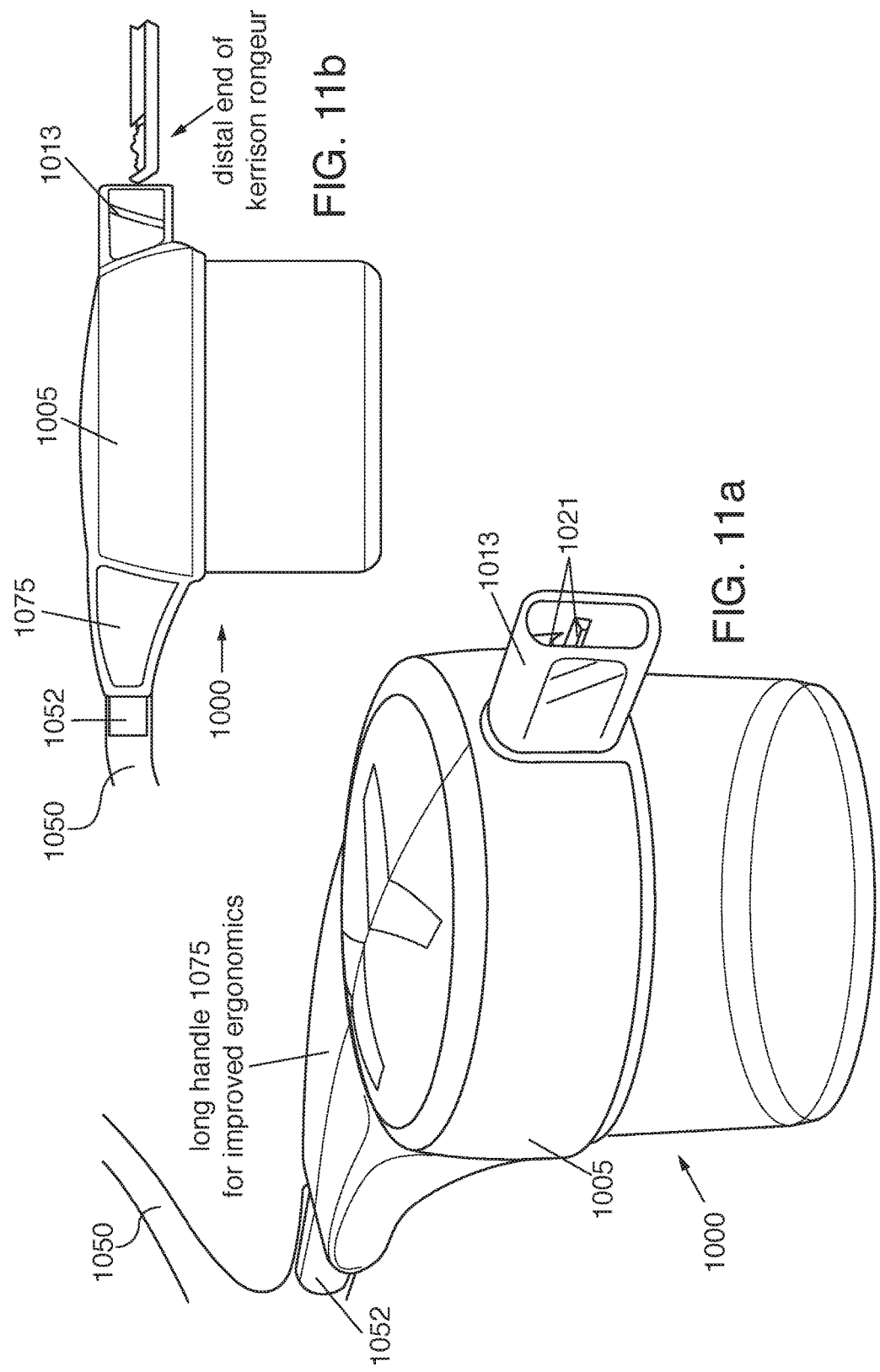

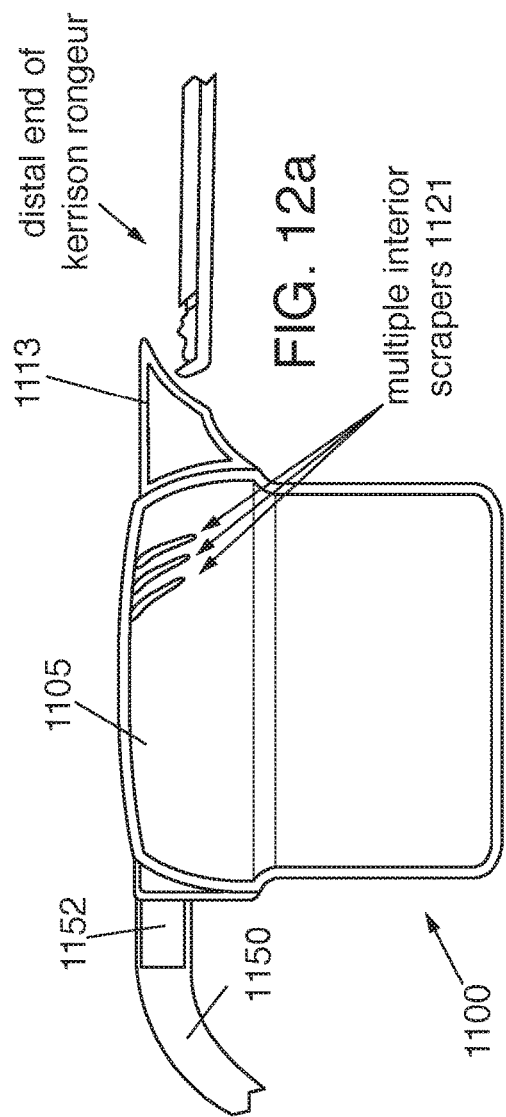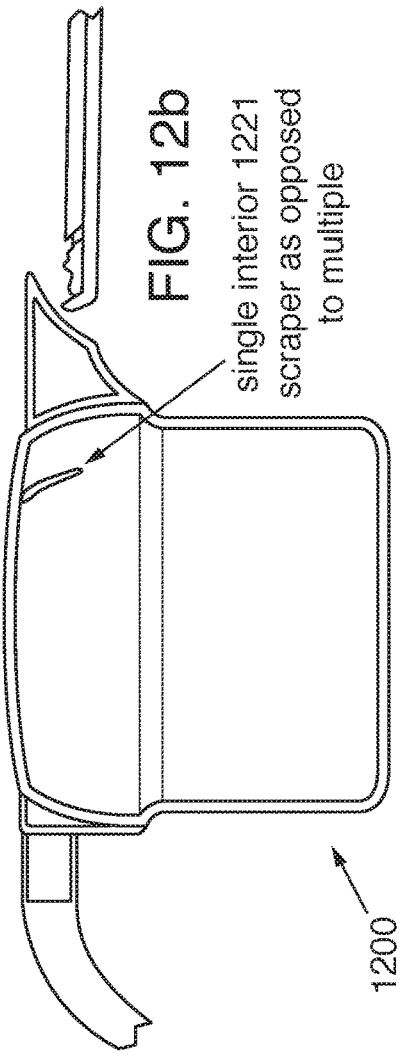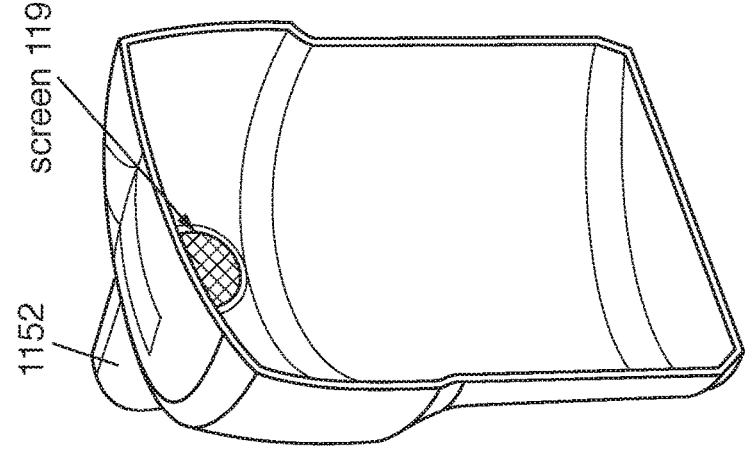

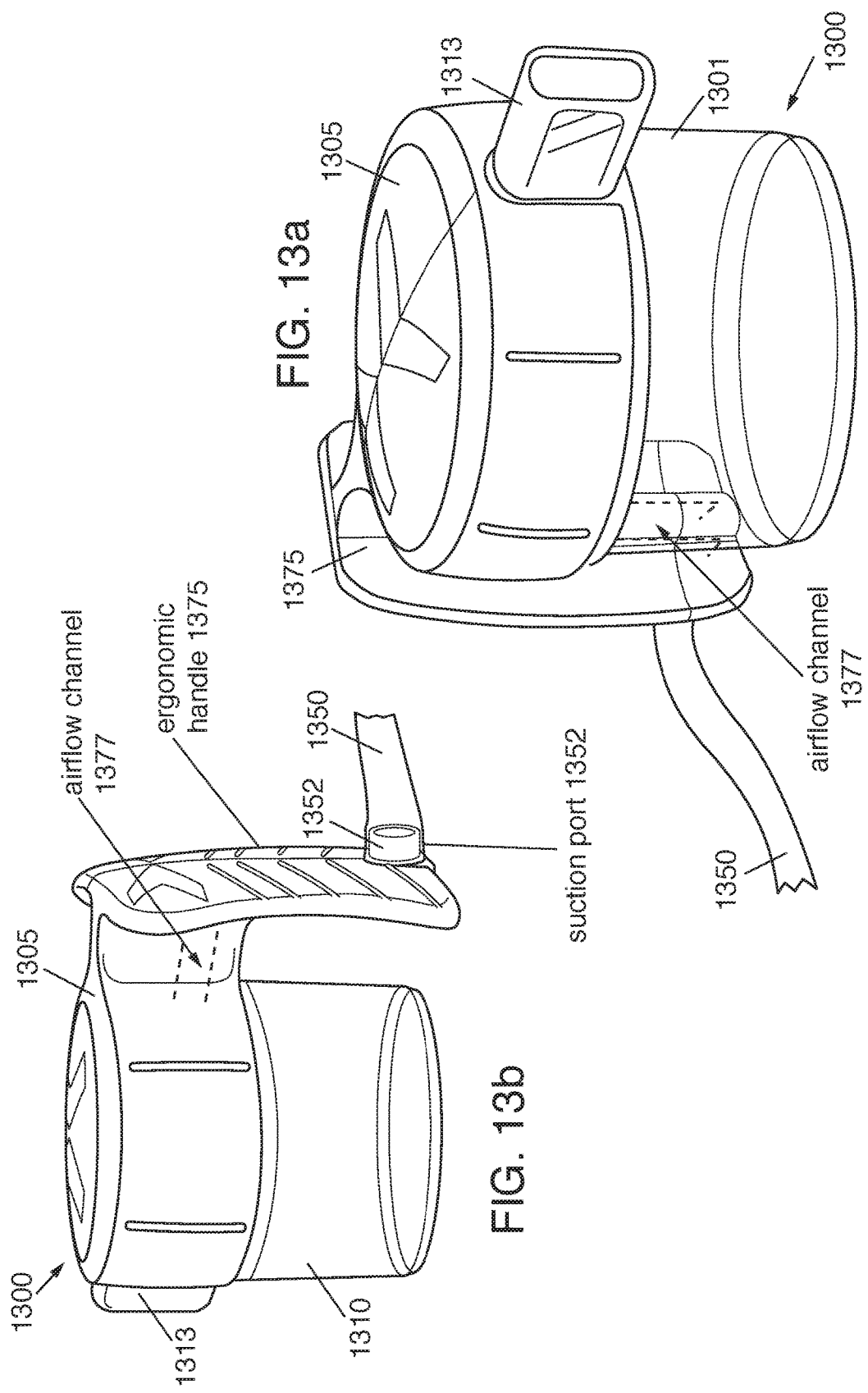

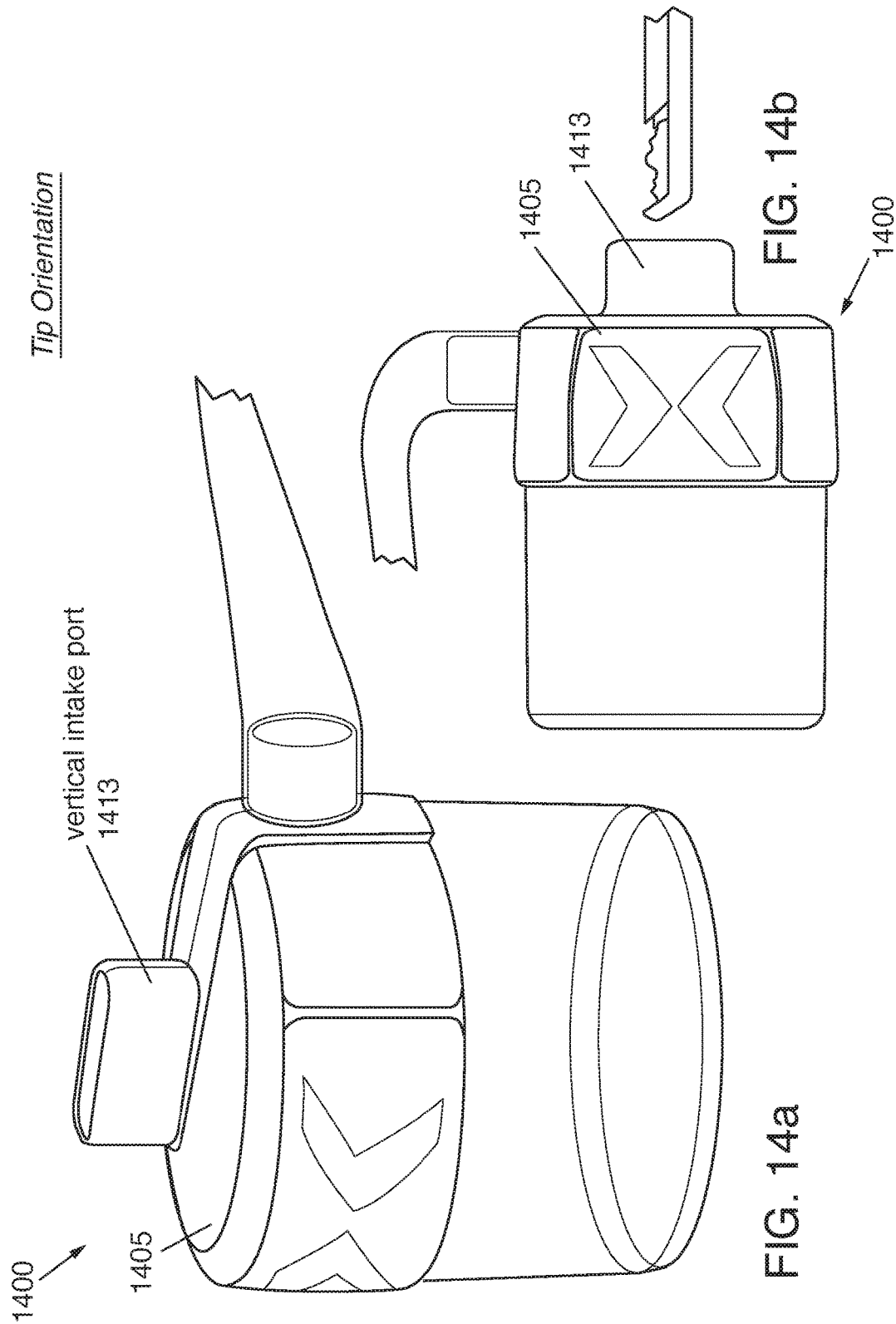

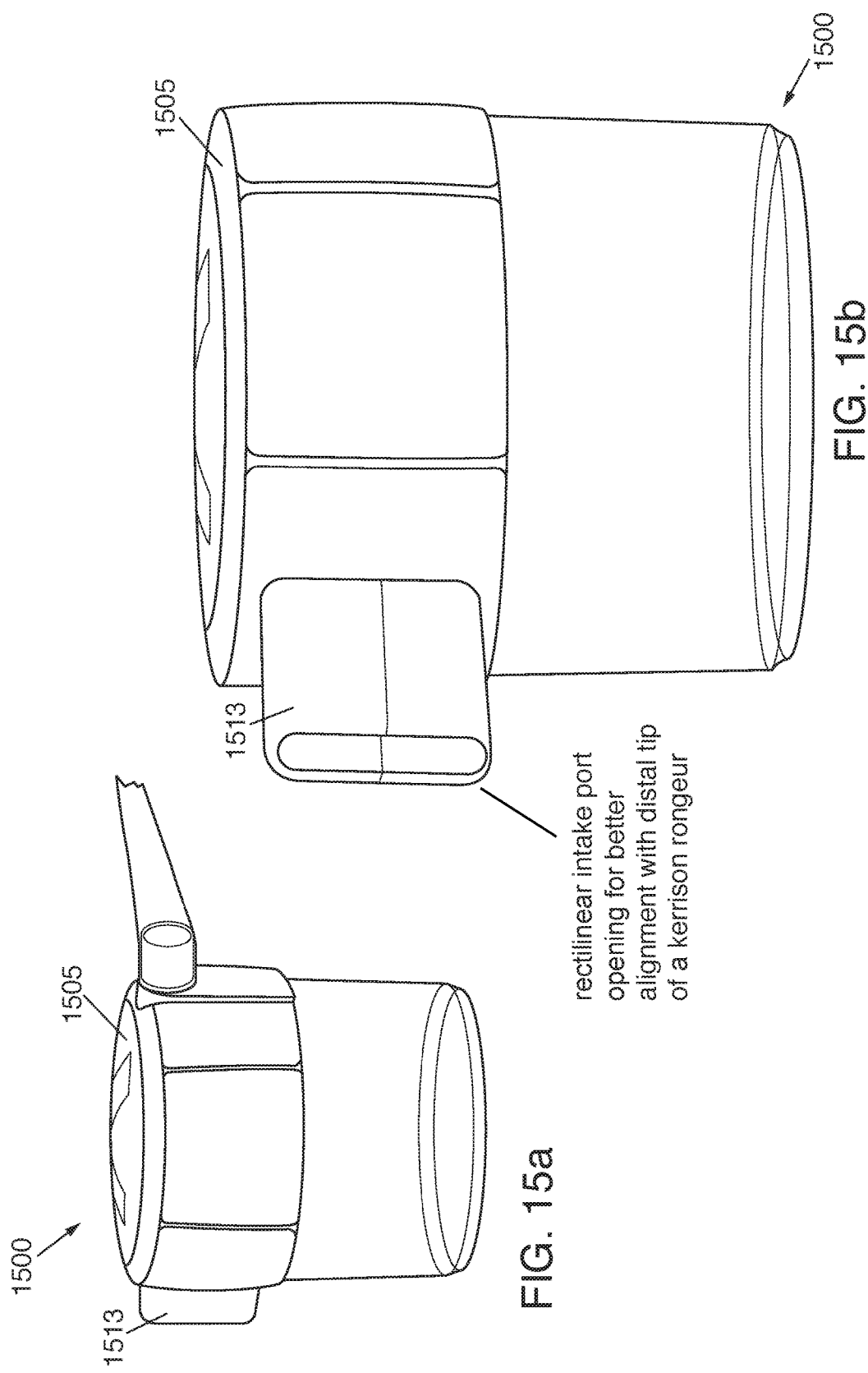

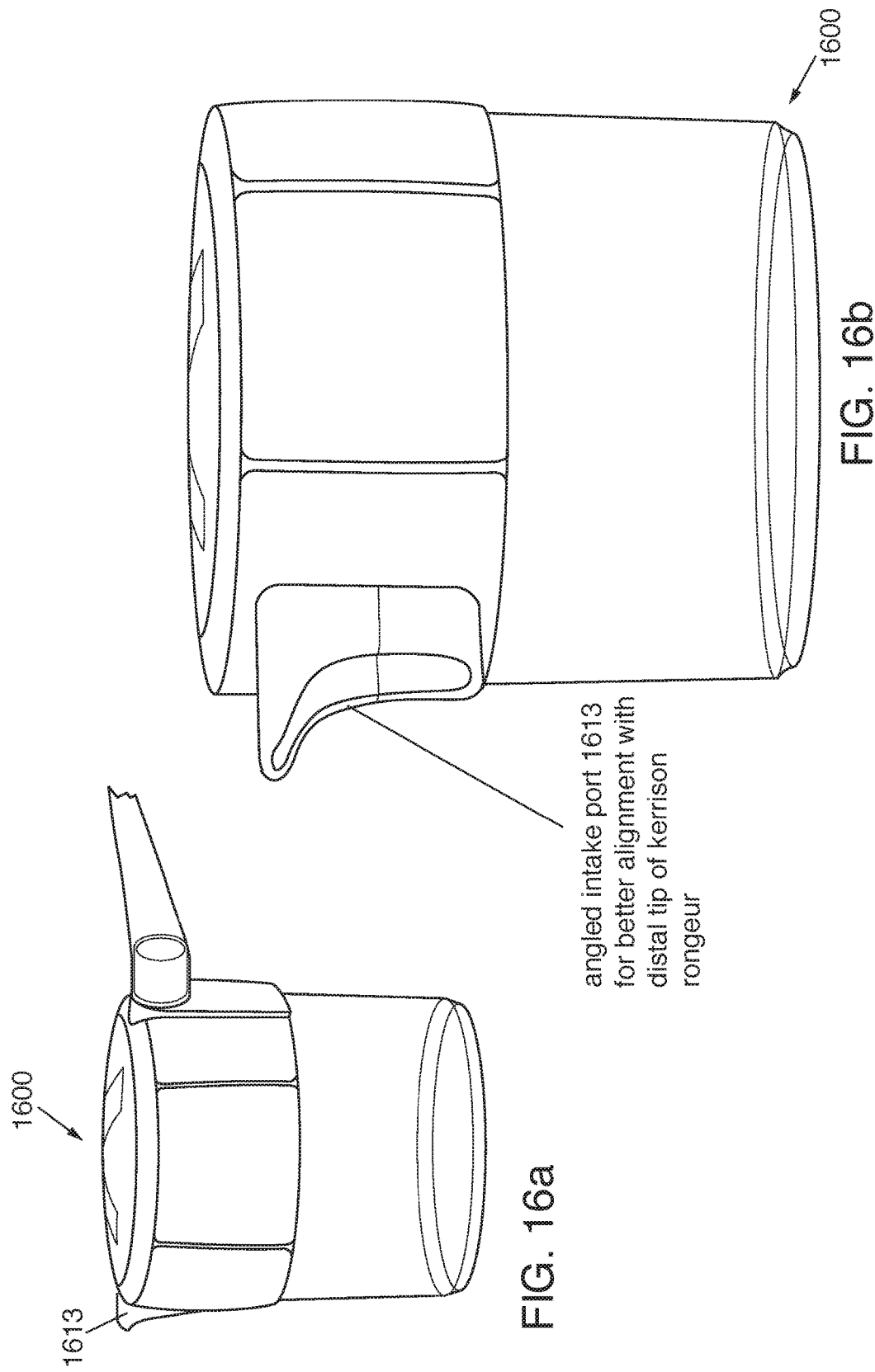

one piece scraper top scraper
Side scraper brushes

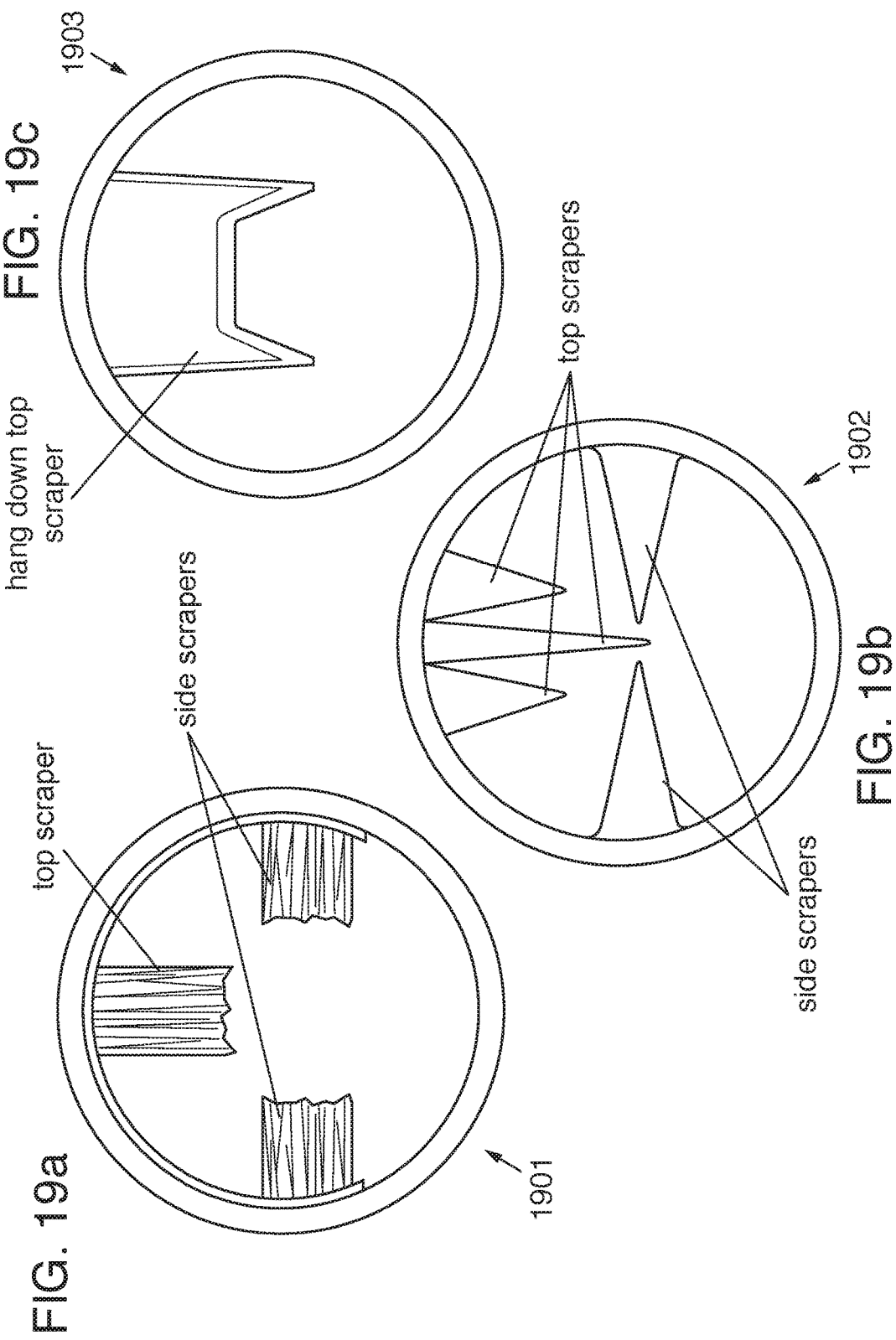

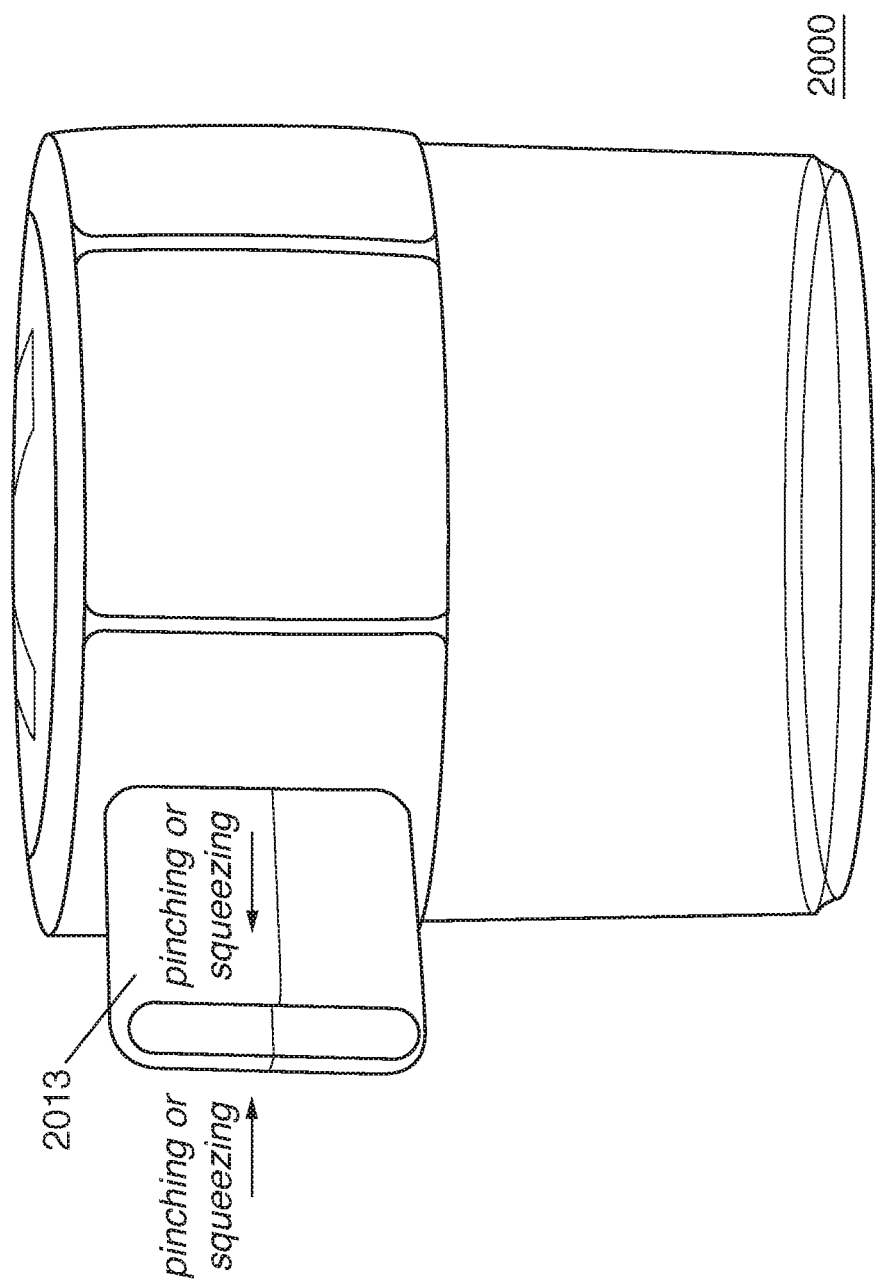

FIG. 21a

| Element | Path | Orientation to Path |
|---|---|---|
| Brush | Axial | Tangent |
| Wiper (soft) | Radial | Axial |
| Wiper (Hard) | Rotational | Axial |
| Pressure (air) | | |
| Suction | | |

FIG. 21b

| Element | Path | Orientation to Path |
|---|---|---|
| Brush | Axial | Tangent |
| Brush | Radial | Tangent |
| Brush | Rotational | Tangent |
| Brush | Axial | Axial |
| Brush | Radial | Axial |
| Brush | Rotational | Axial |
| Wiper (soft) | Axial | Tangent |
| Wiper (soft) | Radial | Tangent |
| Wiper (soft) | Rotational | Tangent |
| Wiper (soft) | Axial | Axial |
| Wiper (soft) | Radial | Axial |
| Wiper (soft) | Rotational | Axial |
| Wiper (Hard) | Axial | Tangent |
| Wiper (Hard) | Radial | Tangent |
| Wiper (Hard) | Rotational | Tangent |
| Wiper (Hard) | Axial | Axial |
| Wiper (Hard) | Radial | Axial |
| Wiper (Hard) | Rotational | Axial |

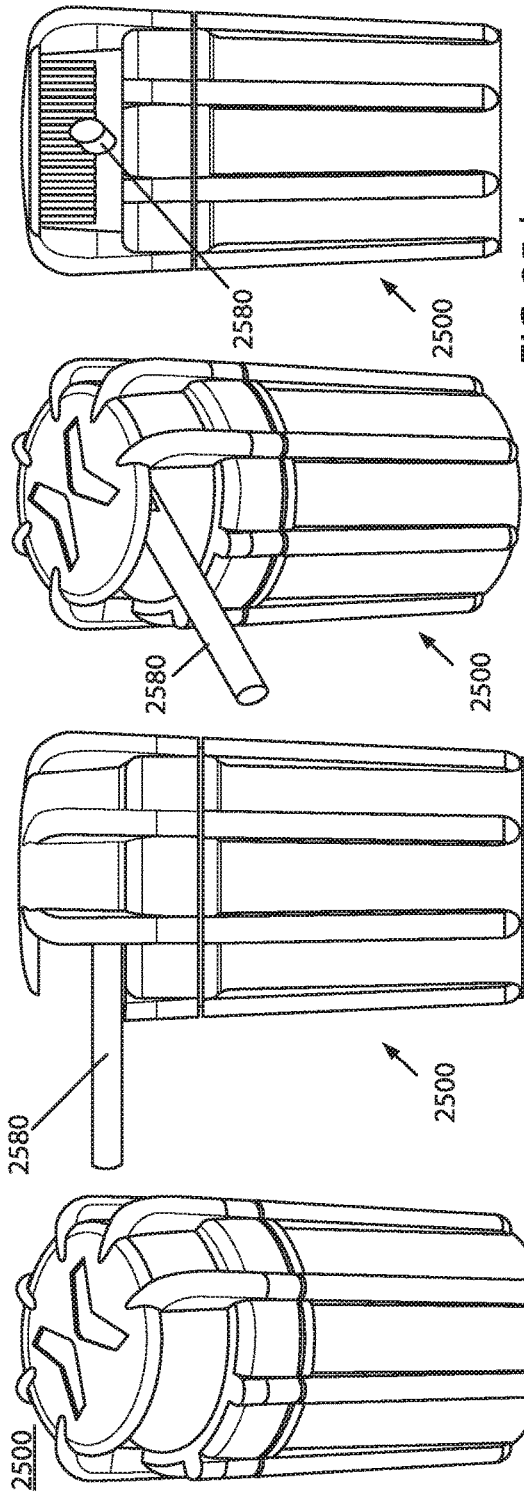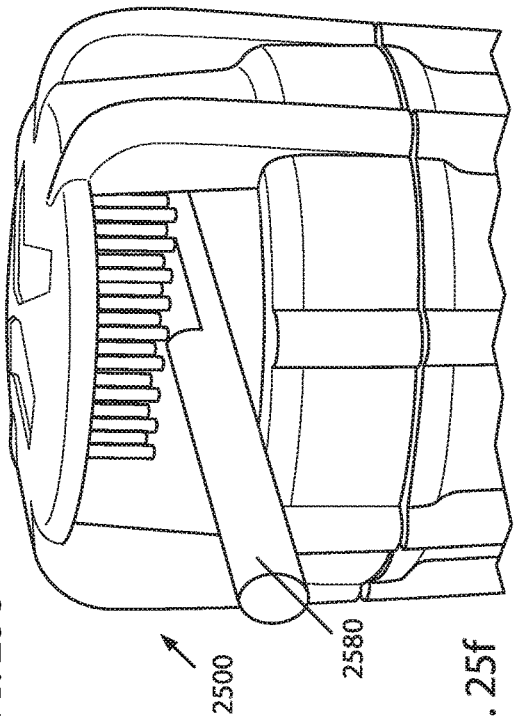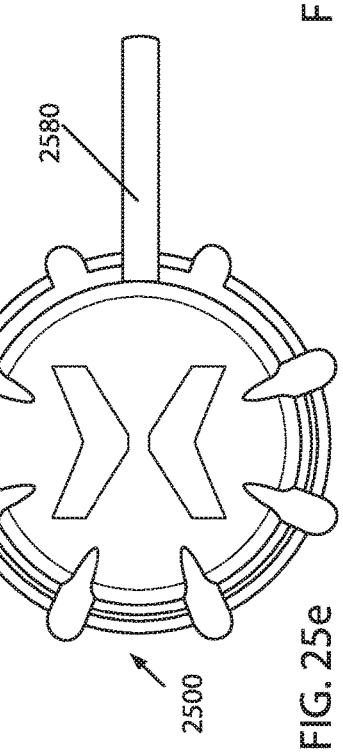
FIG. 25a  FIG. 25b  FIG. 25c  FIG. 25d  FIG. 25e  FIG. 25f

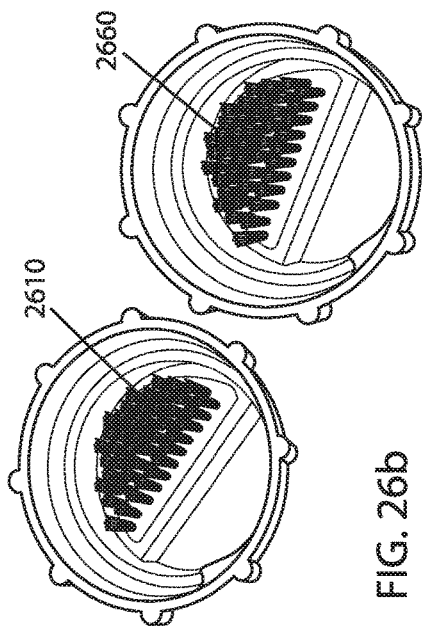
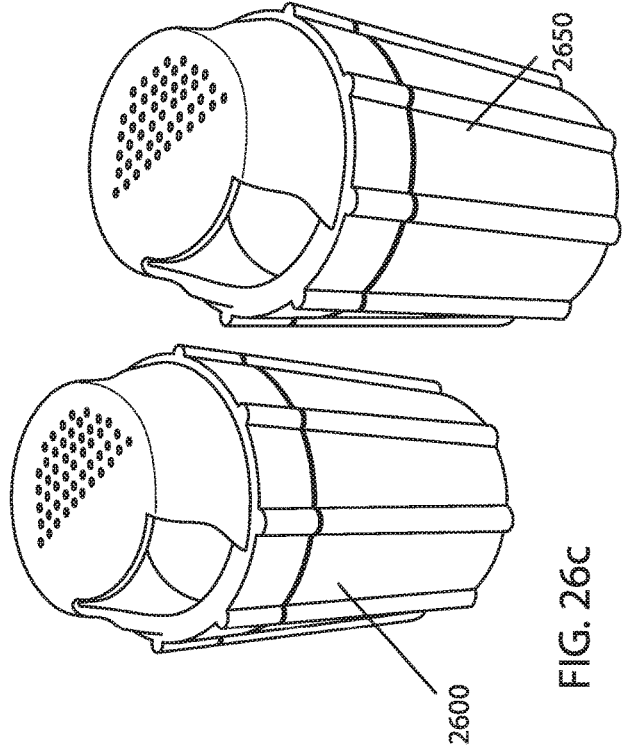
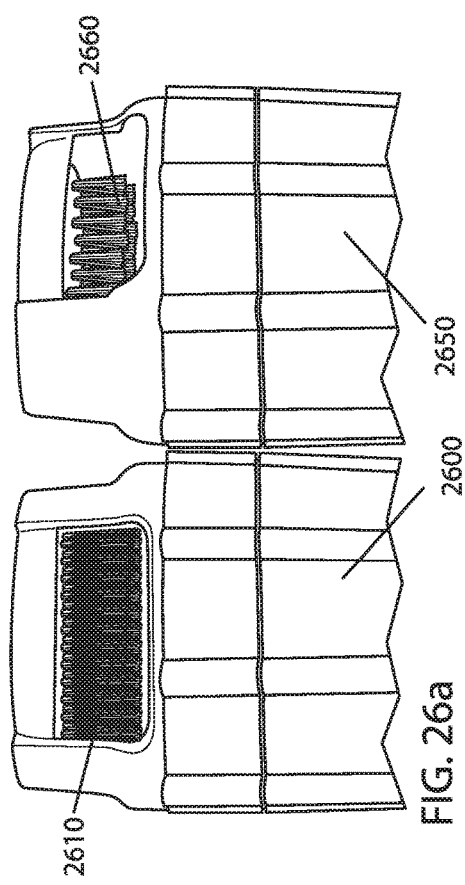
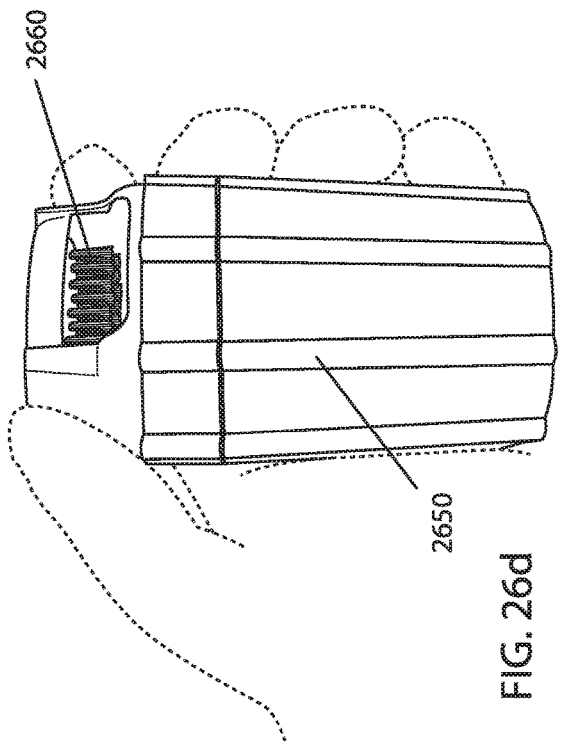
FIG. 26b
FIG. 26c
FIG. 26a
FIG. 26d

COLLECTING AND HARVESTING CUT BONE FROM KERRISON RONGEUR

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to the collection of cut material from a rongeur and, in particular, the collection of bone from a kerrison rongeur.

Rongeurs are surgical instruments for the cutting away of human tissue, and most commonly, cartilage and/or bone. "Kerrison" rongeurs are utilized in spinal surgery to remove bone and to thereby gain access to the spinal canal. rongeurs are well-known within conventional medical knowledge. Patent references disclosing and discussing kerrison rongeurs and their use in surgery include U.S. Pat. Nos. 3,902,498; 5,026,375; 4,722,338; 4,777,940; 4,777,948 and U.S. patent application publication 2003/0216740.

With reference to FIG. 1a, an exemplary prior art kerrison rongeur is illustrated. The kerrison rongeur includes a first jaw member 10 that slides parallel to line A relative to, and on top of, a second jaw member 20. The first jaw member 10 included a distal cutting end having a cutting edge 15. The second jaw member 20 includes a stop 40 for placement beneath the tissue to be cut, which is generally bone or cartilage. A cutting area 30 is defined between the cutting edge 15 of the first jaw member 10 and the stop 40 of the second jaw member 20. The first jaw member 10 includes an open, interior cross-section defining an enclosed area within which the bone tissue is received when cut. Such an exemplary cross-section is illustrated in FIG. 1b. As illustrated, the cross-section of the first jaw member 10 has a generally inverted U shape.

In an exemplary use of a kerrison rongeur, a surgeon places the bone to be cut, such as the leading edge of the lamina of a vertebra, within the open portion of the distal end of the rongeur. The surgeon then squeezes the handle of the rongeur, which advances a moveable jaw member of the rongeur through and amputates a portion of bone. A surgeon may wait until the jaw member becomes full of bone, at which time the rongeur must be completely removed from the surgical site and passed to a scrub nurse or assisting technician for bone removal. The removal from the instrument of the cut portion of bone often requires that the scrub nurse or assisting technician use a small rigid hook, or toothed forceps, and often further requires that the physician temporarily relinquish the instrument entirely to make such bone removal possible. Once cleaned, the instrument is returned to the surgeon who, in returning it to the surgical site, must then reorient himself to the task at hand. This sequence must then be repeated over and over again. Moreover, in a typical spinal fusion, this sequence may require as many as 50 to 100 such repetitions.

Alternatively, a surgeon may present the distal end of the rongeur to a scrub nurse or assisting technician after each cut for removal of the bone, thereby avoiding bone build-up within the jaw member of the rongeur. This can be done without the surgeon relinquishing the rongeur and without the surgeon removing his or her attention and focus from the surgical site. Conventionally, the scrub nurse or assisting technician manually swipes the end of the kerrison rongeur with a sterile material for removing the cut bone. The scrub nurse or assisting technician may repeat the swiping of the cut bone multiple times before harvesting the swiped bone from the material used to perform the swiping. A gauze sponge may be used for swiping. Rather than swiping the bone from the rongeur, a gloved hand may be used by the scrub nurse or assisting technician to directly remove the bone from the rongeur. Thereafter, the harvested bone from the patient may be used in the surgical procedure on the patient, e.g., in autografts.

In view of the foregoing, it is believed that a need exists for a safe, expedient, and efficient way for the cut bone to be removed from the kerrison rongeur and harvested by a scrub nurse or assisting technician without the surgeon relinquishing the kerrison rongeur and without the surgeon having to remove attention and focus from the surgical site. This, and other needs, are believed to be addressed by one or more aspects of the present invention.

SUMMARY OF THE INVENTION

The present invention includes many aspects and features. Moreover, while many aspects and features relate to, and are described in, the context of collection of bone from a kerrison rongeur, which is preferred, the present invention is not limited to only such use, as will become apparent from the following summaries and detailed descriptions of aspects, features, and one or more embodiments of the present invention.

Accordingly, in one aspect of the present invention, a collector used to collect cut bone comprises: a container body defining an interior containment space for receiving and retaining collected bone, and having at least one open end for access and removal of collected bone from the interior containment space; and a cap in covering relation to the open end of the container body such that access to the interior containment space for removal of collected bone is inhibited. The collector comprises an intake port defining an opening for receiving therein a distal end of a kerrison-type rongeur for collecting cut bone from a cutting area thereof, and the cap comprises at least one scraper for engaging and dislodging cut bone from the cutting area of the distal end of the rongeur when received within the intake port.

In a feature of this aspect, the collector defines a passage through which cut bone dislodged by a scraper from the cutting area of the distal end of the rongeur is received within the interior containment space.

In additional features, the cap comprises a stop by which the extent to which the distal end of the rongeur received within the intake port is limited; and the stop is located at a spacing relative to the intake port such that, upon receipt of the distal end of the rongeur and abutment thereof with the stop, the one or more scrapers when actuated extend over and cover the distal end of the rongeur proximate the cutting area in which cut bone would be found.

In another feature, the container body comprises a stop by which the extent to which the distal end of the rongeur received within the intake port is limited.

In additional features, one or more of which may or may not be mutually exclusive: the collector further comprises a stop by which the extent to which the distal end of the rongeur received within the intake port is limited; the stop comprises a depressible button; the depressible button, when depressed, blocks the passage and inhibits receipt of dislodged bone within the interior containment space; and wherein the depressible button, when not depressed, does not inhibit receipt of dislodged bone within the interior containment space; the stop comprises a wall; the wall blocks the passage and inhibits receipt of dislodged bone within the interior containment space; and the wall includes an opening therein, the wall being movable between a first position in which the opening aligns with the passage and the wall does not inhibit receipt of dislodged bone within the interior containment space, dislodged bone passing through the opening in the wall, and a second position in which the opening is out of alignment with the passage and the wall inhibits receipt of dislodged bone within the interior containment space.

In additional features, one or more of which may or may not be mutually exclusive: the cap is detachable from the container body such that access to the interior space for removal of collected bone retained therein is uninhibited by the cap; the cap is attached to the container body in a frictional fit engagement; the cap is attached to the container body in a thread engagement; and the cap screws onto the container body.

In another feature, a portion of the cap is rotatable relative both to the container body and to another portion of the cap.

In additional features, one or more of which may or may not be mutually exclusive: the cap is movable relative to the container body detachable from the container body such that access to the interior space for removal of collected bone retained therein is uninhibited by the cap; a hinge connects the cap to the container body for movement relative thereto; the collector is disposable; one or more components of the collector are disposable; and one or more components of the collector are designed to be sterilized for reuse with different patients in different procedures.

In another feature, the collector is configured to collect cut bone from a kerrison rongeur.

In another feature, the collector is hand-held and lightweight.

In additional features, one or more of which may or may not be mutually exclusive: the container body comprises a generally elongate body or tube having opposite open-ends, wherein the cap comprises a first end cap covering a first of the opposite open-ends of the container body, and further comprising a second end cap covering a second of the opposite open-ends of the container body; and the first and second end caps are generally cylindrical in shape and are axially-aligned along a longitudinal axis of the collector.

In another feature, the one or more scrapers comprise a single scraper, the only one of which that is included in the collector.

In another feature, the one or more scrapers comprise more than one scraper.

In another feature, one of the one or more scrapers comprises bristles.

In another feature, one of the one or more scrapers comprises a brush.

In another feature, one of the one or more scrapers comprises a protuberance.

In another feature, one of the one or more scrapers comprises a barb.

In another feature, one of the one or more scrapers comprises a finger.

In another feature, one of the one or more scrapers is flexible and resilient, and sufficiently rigid so as to hold form when not engaged by the distal end of the rongeur and deflecting and bending upon abutment by and engagement with the distal end of the rongeur.

In another feature, one of the one or more scrapers is made from metal.

In another feature, one of the one or more scrapers is made from polypropylene.

In another feature, the one or more scrapers extend from an underside of the cap toward the interior containment space.

In another feature, the one or more scrapers not are located within the intake port.

In additional features, one or more of which may or may not be mutually exclusive: the one or more scrapers are located within the intake port; and the intake port is squeezable and springy such that the intake port can be squeezed by hand causing the one or more scrapers to enter to cutting area of a kerrison rongeur received within the intake port for dislodging bone carried therein.

In another feature, the container body comprises an opaque wall portion and a transparent wall portion.

In additional features, one or more of which may or may not be mutually exclusive: the container body comprises a movable panel; the panel is connected by a hinge for pivoting movement; and the panel is removable.

In another feature, the intake port is located in the container body.

In another feature, the intake port is located in a side wall of the container body generally halfway in-between opposite ends of the container body.

In another feature, the intake port is located in the cap.

In another feature, the intake port comprises a large, wide opening in the side of the cap configured to receive the tip of a rongeur of various conventional sizes.

In additional features, one or more of which may or may not be mutually exclusive: the intake port is located on the top of the cap; the top of the cap defines a funnel-shaped surface with the intake opening at the center thereof; the top of the cap defines a flange for catching dislodged bone when the collector is turned sideways and the distal end of the rongeur is received within the intake port; the cap defines a cutout for visual alignment of the collector when receiving the distal end of the rongeur; and the cap comprises a protuberance for visual alignment of the collector when receiving the distal end of the rongeur.

In another feature, the intake port is located on a side of the cap.

In another feature, the intake port includes a hawk bill profile.

In additional features, the intake port defines a scraping tip; and the scraping tip is rigid.

In another feature, the intake port includes an angular profile.

In another feature, the intake port includes a rounded profile.

In additional features, one or more of which may or may not be mutually exclusive: the one or more scrapers are manually movable into a position for engaging and dislodging cut bone from the cutting area of the distal end of the rongeur when received within the intake port; the one or more scrapers comprise at least two opposed scrapers that are manually moved in directions toward one another so as to converge within the cutting area of the distal end of the rongeur when received within the intake port; opposite ends of the collector each includes a depressible portion by which, when depressed, the opposed scrapers are manually moved so as to converge within the cutting area of the distal end of the rongeur when received within the intake port; the depressible portion is spring-biased against depression; the opposed scrapers are rotatable about a longitudinal axis of the container body by manual rotation of the depressible portions of the end caps; and the one or more scrapers comprise a scraper that is manually moved within the cutting area of the distal end of the rongeur when received within the intake port by twisting of the cap on the container body.

In additional features, one or more of which may or may not be mutually exclusive: the cap further comprises a handle; and the handle extends generally downwardly proximate a side of the container body, a distal end of the handle being located closer to an end of the container body opposite the cap.

In additional features, one or more of which may or may not be mutually exclusive: the collector further comprises a suction port for suctioning dislodged bone into receipt within the interior containment space of the container body; the cap defines the suction port; the suction port is located on a side of the cap; the cap further comprises a handle; the suction port is located on the handle; the handle extends generally downwardly proximate a side of the container body, a distal end of the handle being located closer to an end of the container body opposite the cap; and the suction port is located at the distal end of the handle, with an interior passage extending through the handle from the suction port and opens into the interior containment space defined by container body.

In another feature, the collector is configured to be held in a sideways position when used to collect cut bone from a kerrison rongeur.

In yet another feature, the container body includes an interior containment space having a graduated containment volume of thirty cubic centimeters.

In another feature, the collector is configured to be held in a horizontal position when used to collect cut bone from a kerrison rongeur, the cap and the container body being horizontally oriented relative to one another.

In another feature, the collector is configured to be held in an upright position when used to collect cut bone from a kerrison rongeur.

In another feature, the collector is configured to be held in a vertical position when used to collect cut bone from a kerrison rongeur, the cap and the container body being vertically oriented relative to one another with the cap being at a vertical elevation greater than the container body.

In another feature, the container body is box-shaped with generally rectangular sides and wherein the cap comprises rectangular sides.

In another feature, the container body is transparent. Preferably the container body is made from an inert material conventionally used with medical containers for holding human tissue for use in a body. In at least some embodiments, the container body comprises a molded plastic body, and the cap comprises a molded plastic body.

In another aspect, a device for collecting autologous bone fragments comprises a container and a cap. The container comprises a visibly transparent material and may include graduations to indicate volume of collected tissue comprising bone in the container. The cap is attachable to the container by way of threads on both the container and the cap, whereby the cap screws onto the container. Preferably the cap is symmetrical with the exception of an opening that is wide with respect to the diameter of the cap. The opening is configured to allow the passage of the tip of a kerrison rongeur of multiple sizes along with bone and other tissue matter carried on the tip. The cap further comprises a brush disposed on the underside of the cap facing the interior of the container. The brush comprises a plurality of bristles which may comprise individual monofilament bodies. Moreover, the bristles preferably comprise a material that is absorbable by the human body; a bio-absorbable bristle is preferred in the event that a bristle becomes dislodged and mixed with the harvested matter from the tip of the kerrison rongeur, and thereafter is inadvertently inserted into the patient.

In use, the tip of the kerrison rongeur carrying the matter cut from the patient is inserted through the opening of the cap, and the brush is used to dislodge the matter from the kerrison tip whereby the matter falls into the interior space of the container and is thereby collected. Dislodging the matter may be effected by moving the kerrison tip upward away from the container and into the brush in the underside of the cap and/or translating the kerrison tip perpendicularly to the length of the kerrison body. Additional or alternative movements can be used such as, for example, rotating the brush relative to the tip of the kerrison rongeur for dislodging the cut matter from the tip. The kerrison rongeur thereafter is removed for further use. Later when the harvested matter is needed, the cap is unscrewed from the container and the matter, i.e., bone in preferred implementations, is retrieved from the container.

In another aspect, a kit comprises an aforementioned collector and a rongeur, wherein the collector is configured to collect cut bone from the rongeur of the kit.

Another aspect comprises a method of using an aforementioned collector to collect cut bone.

Another aspect comprises a method of using an aforementioned collector to collect cut bone from a rongeur.

Another aspect comprises a method of using an aforementioned collector to collect cut bone from a kerrison rongeur.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings.

FIG. 1b illustrates a cross-sectional shape of the first jaw member 10 of the kerrison rongeur of FIG. 1a.

FIG. 2a is a perspective view of a collector used to collect cut bone from a kerrison rongeur in accordance with a first embodiment of the present invention, wherein the collector is illustrated in a generally vertical orientation.

FIG. 2b is a perspective view illustrating a sequence of steps for using the collector of FIG. 2a in collecting bone from a kerrison rongeur, wherein the collector is illustrated in a generally horizontal orientation.

FIG. 2c is a perspective view of a portion of the collector of FIG. 2a after bone has been collected from a kerrison rongeur.

FIG. 3a is a perspective view of a collector used to collect cut bone from a kerrison rongeur in accordance with a second embodiment of the present invention, wherein the collector is illustrated in a generally vertical orientation.

FIG. 3b is a perspective view illustrating a sequence of steps for using the collector of FIG. 3a in collecting bone from a kerrison rongeur, wherein the collector is illustrated in a generally horizontal orientation.

FIG. 3c is a top plan view of a cap of the collector of FIG. 3a.

FIG. 3d is a side elevational view of the cap of the collector of FIG. 3a.

FIG. 4a is a perspective view representative of a sequence of steps for using another collector in accordance with a third embodiment of the present invention, wherein the collector is illustrated in a generally horizontal orientation receiving the distal end of a kerrison rongeur.

FIG. 4b is a top plan view of the collector and distal tip of the kerrison rongeur of FIG. 4a.

FIG. 5a a perspective view of a collector used to collect cut bone from a kerrison rongeur in accordance with another embodiment of the present invention, wherein the collector is illustrated in a generally vertical orientation.

FIG. 5b is a perspective view illustrating a sequence of steps for using the collector of FIG. 5a in collecting bone from a kerrison rongeur, wherein the collector is illustrated in a generally horizontal orientation with the distal end of the kerrison rongeur being received within the collector.

FIG. 5c is a side elevational view of an alternative embodiment to that of FIG. 5a, in which the height of the collector is less than that shown in FIG. 5a, the collector of FIG. 5c thus having a shorter profile.

FIG. 6a is a perspective view of a collector used to collect cut bone from a kerrison rongeur in accordance with another embodiment of the present invention, wherein the collector is illustrated in a generally horizontal orientation.

FIG. 6b is a side elevational view of the collector of FIG. 6a.

FIG. 7a is a perspective view of a collector used to collect cut bone from a kerrison rongeur in accordance with another embodiment of the present invention, wherein the collector is illustrated in a generally horizontal orientation.

FIG. 7b is a side elevational view of the collector of FIG. 7a.

FIG. 7c is another side elevational view of the collector of FIG. 7a.

FIG. 8a is a perspective view of a collector used to collect cut bone from a kerrison rongeur in accordance with another embodiment of the present invention, wherein the collector is illustrated in a generally horizontal orientation.

FIG. 9a is a perspective view of a collector used to collect cut bone from a kerrison rongeur in accordance with another embodiment of the present invention, wherein the collector is illustrated in a generally horizontal orientation.

FIG. 9b is a perspective view of part of a release mechanism of the collector of FIG. 9a.

FIG. 9c is a schematic illustration representing the arrangement and operation of the release mechanism of FIG. 9b.

FIG. 10a is a perspective view of a collector used to collect cut bone from a kerrison rongeur in accordance with yet another embodiment of the present invention, wherein the collector is illustrated in a generally vertical orientation and includes a suction tube attached thereto.

FIG. 10b is a side plan view of the collector of FIG. 10a and includes a close-up, cross-sectional view of an intake port of the collector of FIG. 10a within which a distal tip of a kerrison rongeur is received.

FIG. 11a is a perspective view of a collector used to collect cut bone from a kerrison rongeur in accordance with yet another embodiment of the present invention, wherein the collector is illustrated in a generally vertical orientation and includes a suction tube attached thereto.

FIG. 11b is a side plan view of the collector of FIG. 11a.

FIG. 12a is a side plan view in cross-section of a collector used to collect cut bone from a kerrison rongeur in accordance with yet another embodiment of the present invention, wherein the collector is illustrated in a generally vertical orientation and includes a suction tube attached thereto, and wherein the collector includes multiple interior scrapers.

FIG. 12b is a side plan view in cross-section of another collector similar to that of FIG. 12a, and differs in that the collector of FIG. 12b includes a single interior scraper.

FIG. 12c is a perspective view in cross-section of a portion of the collector of FIG. 12a illustrating a screen for filtering of outflow from the collector through the suction tube.

FIG. 13a is a perspective view of a collector used to collect cut bone from a kerrison rongeur in accordance with yet another embodiment of the present invention, wherein the collector is illustrated in a generally vertical orientation.

FIG. 13b is another perspective view of an opposite side of the collector as seen in FIG. 13a.

FIG. 14a is a perspective view of a collector used to collect cut bone from a kerrison rongeur in accordance with yet another embodiment of the present invention, wherein the collector is illustrated in a generally vertical orientation.

FIG. 14b is a perspective view illustrating a use of the collector of FIG. 14a in collecting bone from a kerrison rongeur, wherein the collector is illustrated in a generally horizontal orientation with the distal end of the kerrison rongeur about to be received through an intake port of the collector.

FIG. 15a is a perspective view of a collector used to collect cut bone from a kerrison rongeur in accordance with yet another embodiment of the present invention, wherein the collector is illustrated in a generally vertical orientation.

FIG. 15b is another perspective view of an opposite side of the collector as seen in FIG. 15a, wherein the intake port of the collector is better seen.

FIG. 16a is a perspective view of a collector used to collect cut bone from a kerrison rongeur in accordance with yet another embodiment of the present invention, wherein the collector is illustrated in a generally vertical orientation.

FIG. 16b is another perspective view of an opposite side of the collector as seen in FIG. 16a, wherein the intake port of the collector is better seen.

Each of FIGS. 17a-17f illustrates in elevational plan view, taken in cross-section, a shape of an intake port for a collector in accordance with various embodiments of the present invention.

Figure 18C:
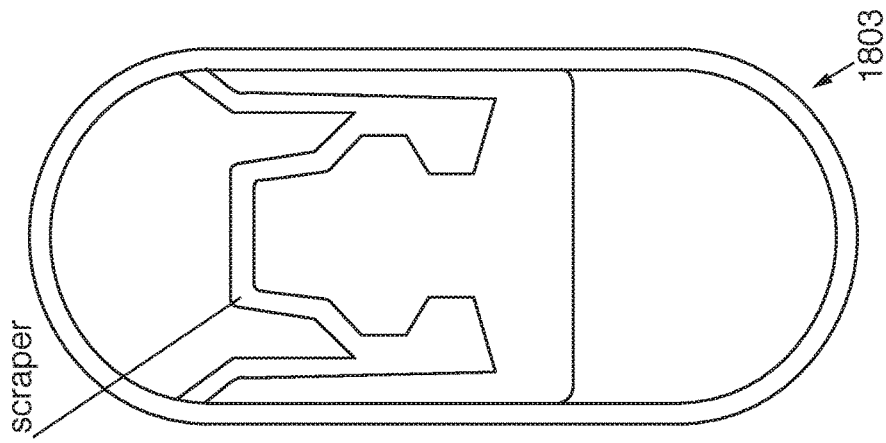
Figure 18B:
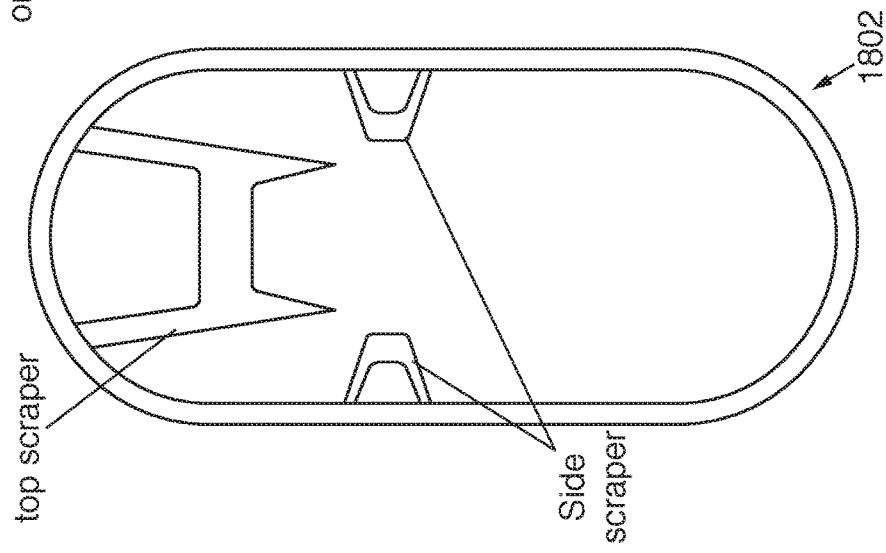
Figure 18A:
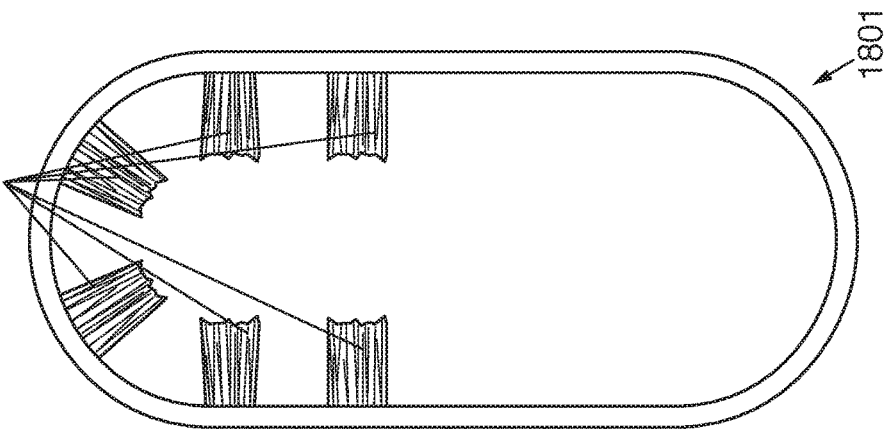

Each of FIGS. 18a-18c illustrates in plan view an opening of an intake port for a collector in accordance with various embodiments of the present invention.

Each of FIGS. 19a-19c illustrates in plan view a generally oval (preferably circular) intake port opening of an intake port for a collector in accordance with various embodiments of the present invention.

FIG. 20 is a perspective view of a collector used to collect cut bone from a kerrison rongeur in accordance with yet another embodiment of the present invention, wherein the collector is illustrated in a generally vertical orientation.

FIG. 21a illustrates a table listing values of properties giving rise to some possible variations between some embodiments of the invention.

FIG. 21b illustrates a table listing some possible combinations of some of the elements of the table of FIG. 21a.

Figure 22G:
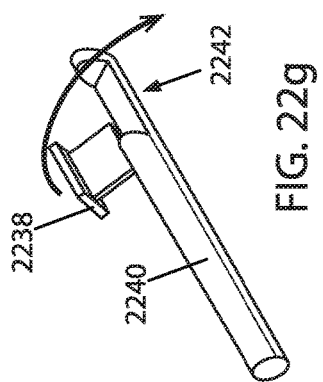
Figure 22D:
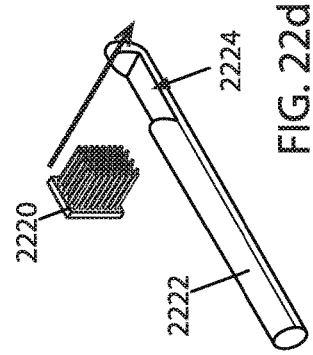
Figure 22E:
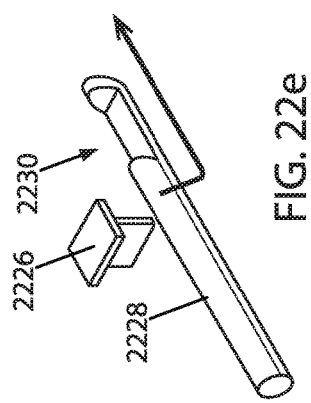
Figure 22F:
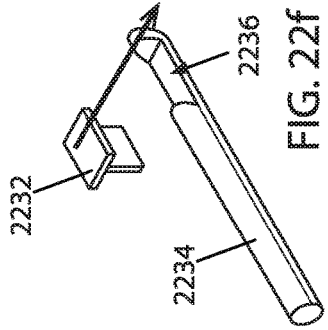
Figure 22A:
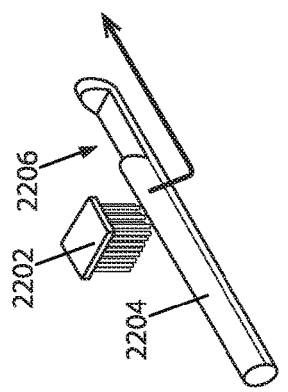

FIG. 22a is a perspective view of a tip and scraper showing path and orientation properties representative of some embodiments of the invention.

Figure 22B:
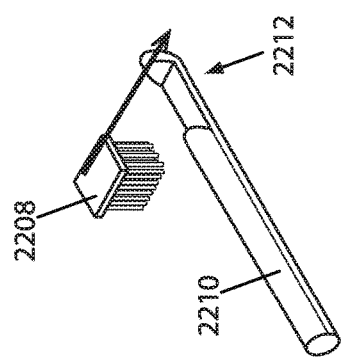

FIG. 22b is a perspective view of a tip and scraper showing path and orientation properties representative of some embodiments of the invention.

Figure 22C:
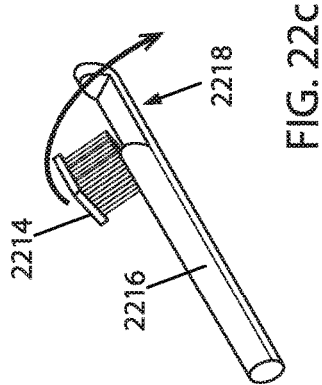

FIG. 22c is a perspective view of a tip and scraper showing path and orientation properties representative of some embodiments of the invention.

FIG. 22d is a perspective view of a tip and scraper showing path and orientation properties representative of some embodiments of the invention.

FIG. 22e is a perspective view of a tip and scraper in the form of a wiper showing path and orientation properties representative of some embodiments of the invention.

FIG. 22f is a perspective view of a tip and scraper in the form of a wiper showing path and orientation properties representative of some embodiments of the invention.

FIG. 22g is a perspective view of a tip and scraper in the form of a wiper showing path and orientation properties representative of some embodiments of the invention.

Figure 23:
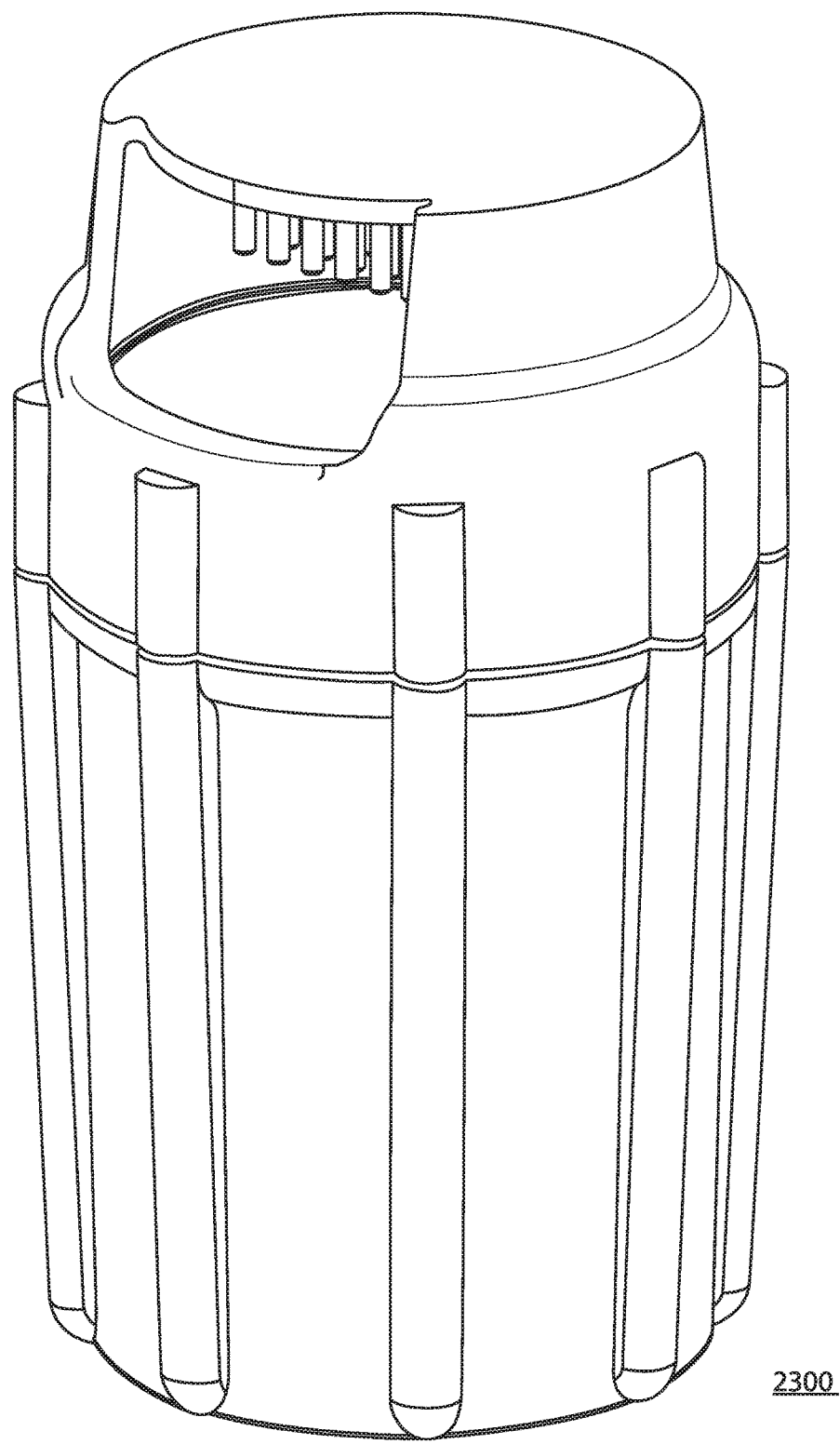

FIG. 23 illustrates a perspective view of a collector in accordance with another embodiment of the invention.

Figure 24A:
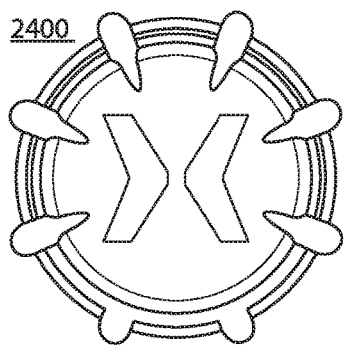

FIG. 24a illustrates a top plan view of a cap of a collector 2400 in accordance with another embodiment of the invention.

Figure 24F:
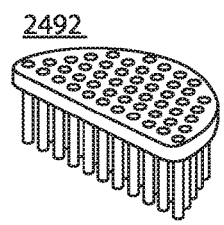
Figure 24C:
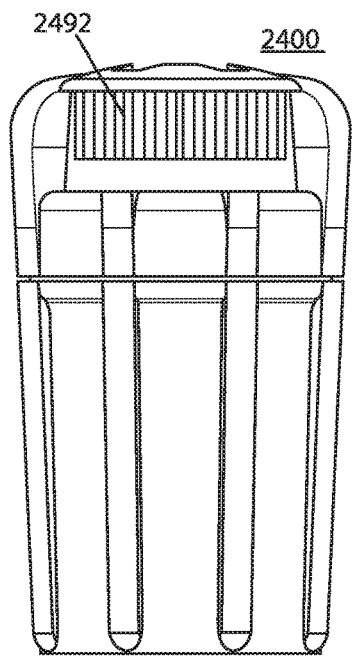
Figure 24B:
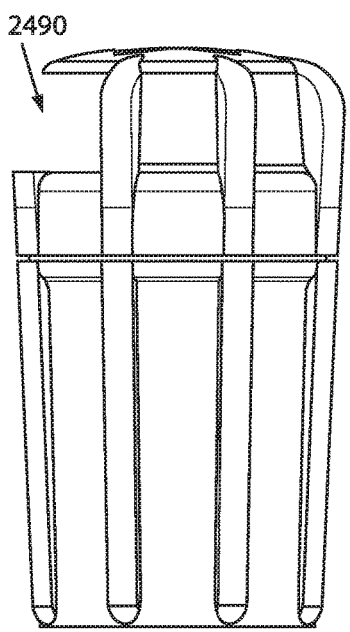

FIG. 24b is a side elevational view of the collector 2400.

FIG. 24c is another side elevational view of the collector 2400.

Figure 24D:
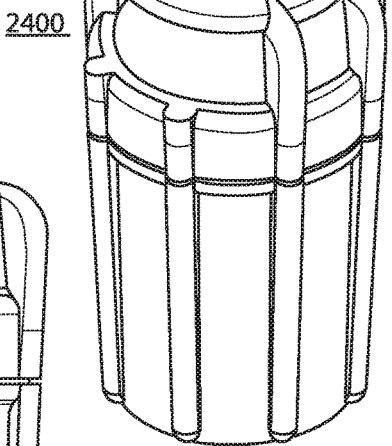

FIG. 24d is a top perspective side view of the collector 2400.

Figure 24E:
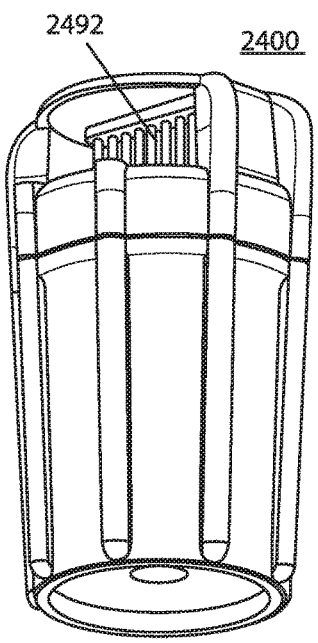

FIG. 24e is a bottom perspective side view of the collector 2400.

FIG. 24f is a perspective view of the scraper of the collector 2400, which scraper is located under and attached to the cap, as seen through the opening in the cap in FIGS. 24c and 24e.

FIG. 25a is a perspective view of a collector in accordance with another embodiment of the invention.

FIG. 25b is a side elevational view of the collector of FIG. 25a, further illustrating a tip of a rongeur inserted into the cap thereof.

FIG. 25c is a perspective view of the collector of FIG. 25a, further illustrating a tip of a rongeur inserted into the cap thereof.

FIG. 25d is another elevational side view of the collector of FIG. 25a, further illustrating a tip of a rongeur inserted into the cap thereof.

FIG. 25e is a top perspective view of the collector of FIG. 25a, further illustrating a tip of a rongeur inserted into the cap thereof.

FIG. 25f is a perspective close-up view of the top of the collector of FIG. 25a with a tip of a rongeur inserted therein, and further illustrating bristles of the brush extending from the underside of the top of the cap downwardly into engagement with the tip of the rongeur.

FIG. 26a is a side-by-side elevational view of the tops of two prototype collectors, each in accordance with a respective embodiment of the invention.

FIG. 26b is a perspective view of the caps of the collectors of FIG. 26a after the caps have been unscrewed from the containers and placed upside down on a surface to expose views of the brushes attached to the underside of the caps.

FIG. 26c is a side-by-side top perspective view of the collectors of FIG. 26a.

FIG. 26d is a side elevational view of one of the collectors of FIG. 26a.

Figure 27:
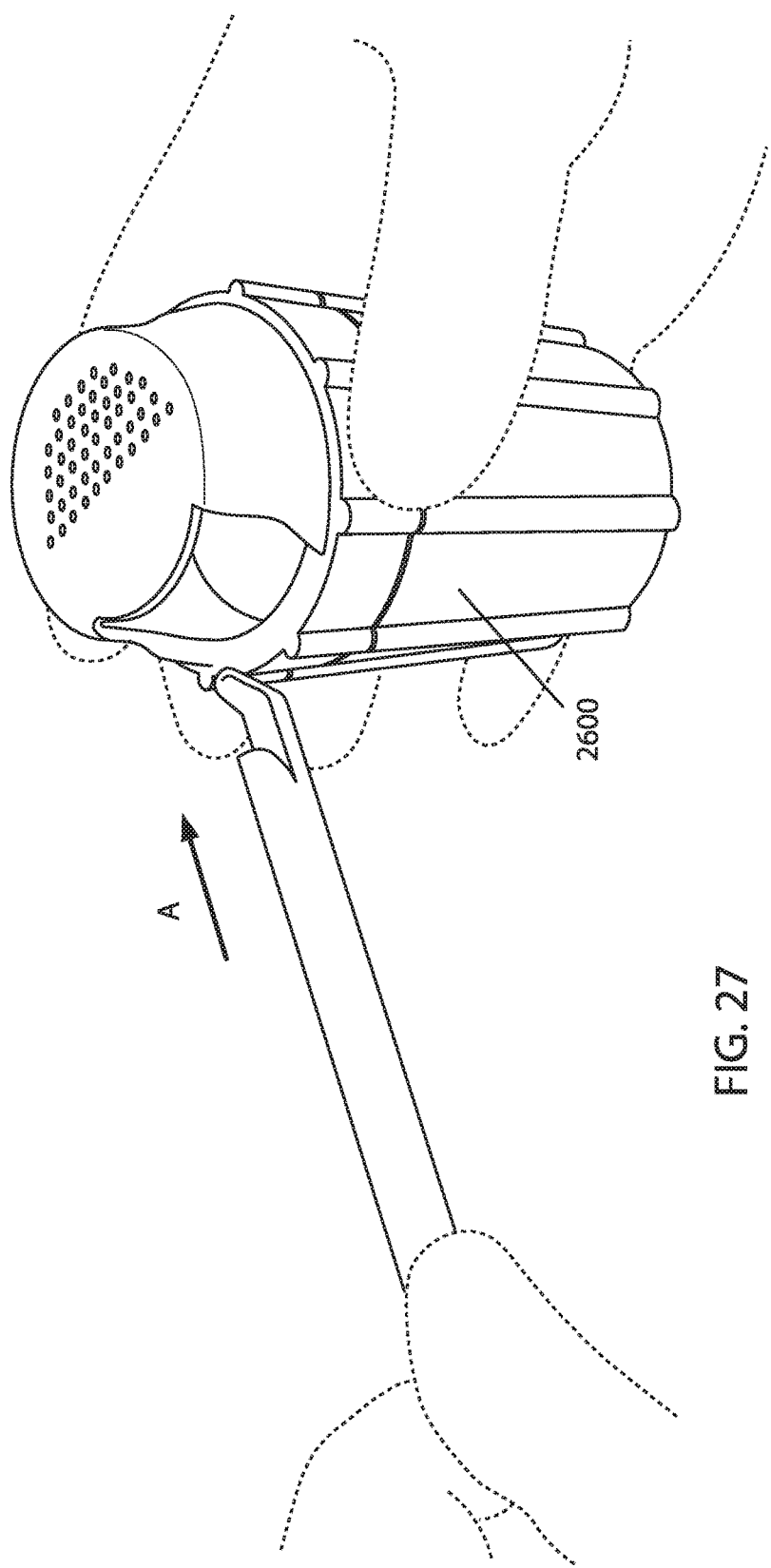

FIG. 27 is a perspective view showing movement of the tip of a rongeur in the direction of arrow A so as to extend through a port of a collector in accordance with an embodiment of the invention.

FIG. 28a is another perspective view showing the tip of the rongeur of FIG. 27 received within the cap of the collector of FIG. 27.

FIG. 28b is another perspective view also showing the tip of the rongeur of FIG. 27 received within the cap of the collector of FIG. 27.

Figure 29:
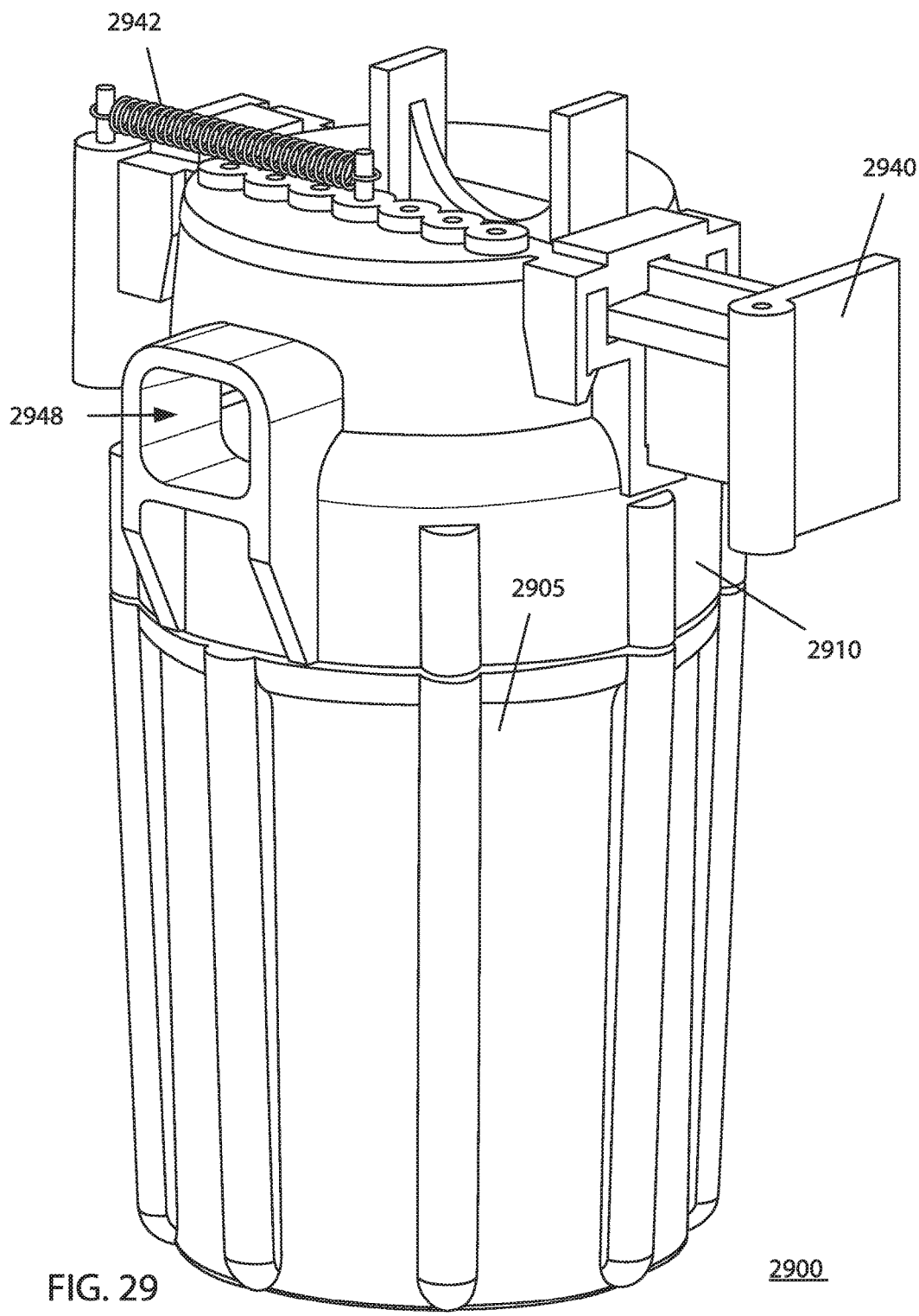

FIG. 29 is a perspective side view of a collector in accordance with yet another embodiment of the invention.

Figure 30:
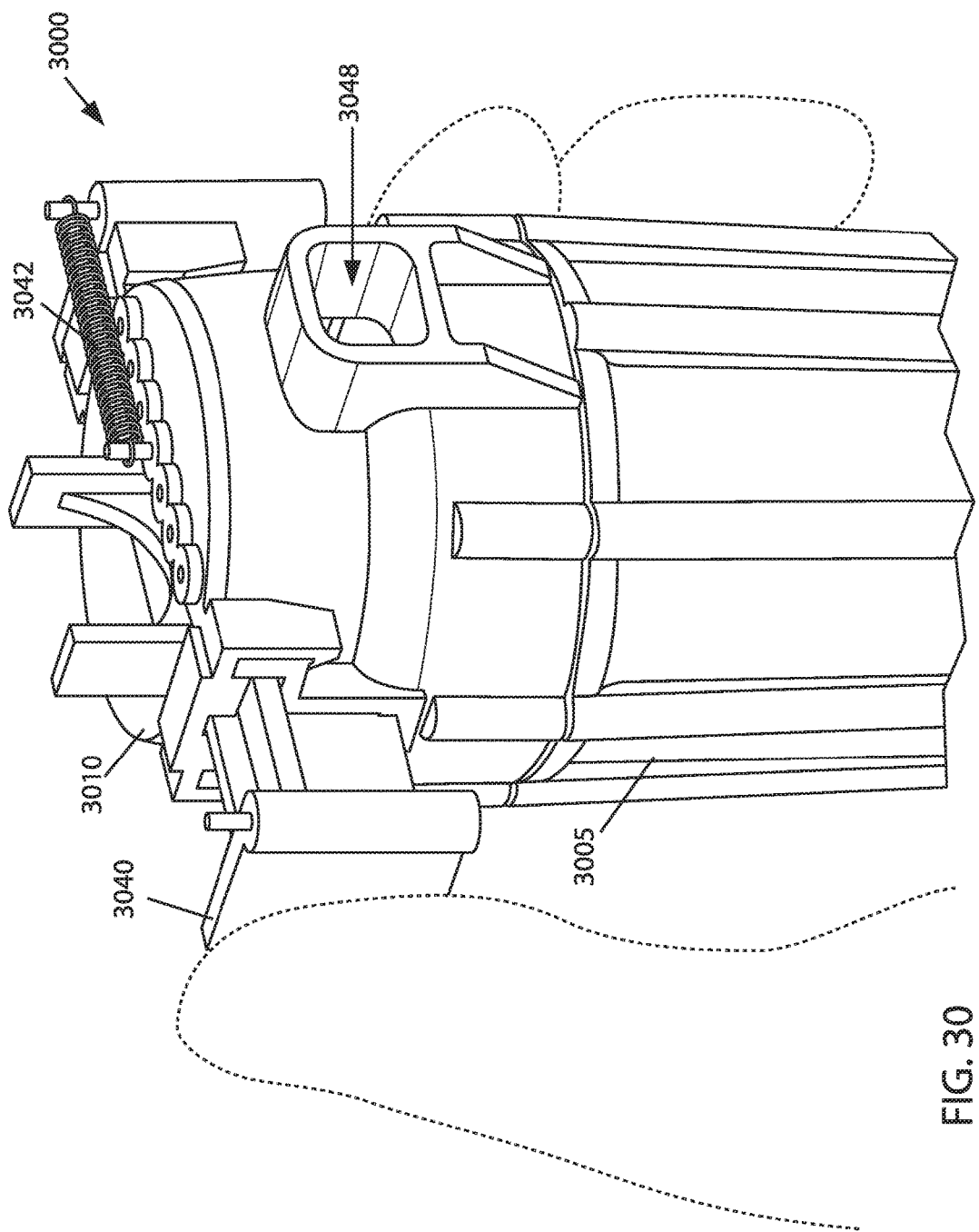

FIG. 30 is a perspective side view of a prototype collector representative of the embodiment of FIG. 29.

Figure 31:
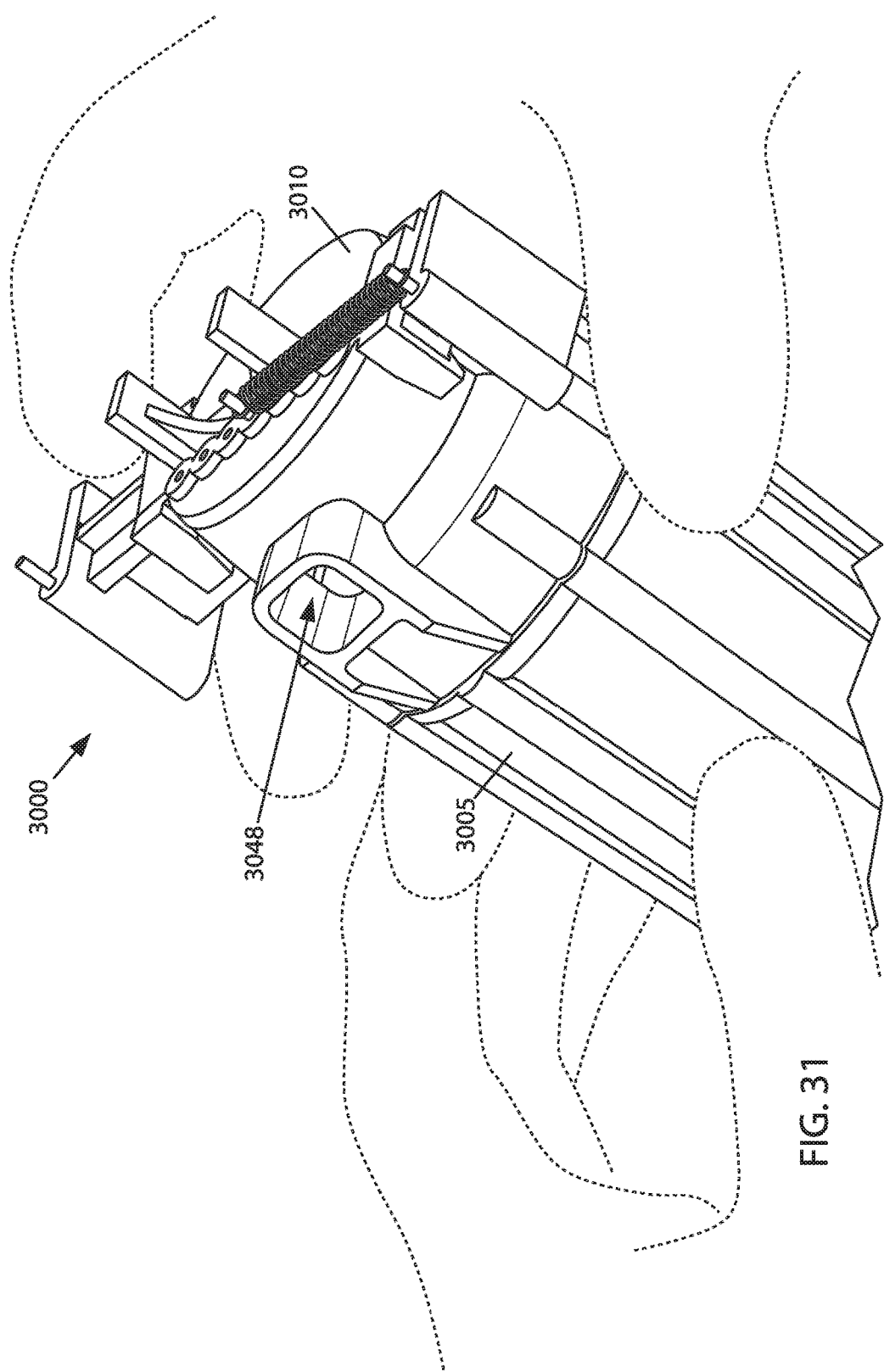

FIG. 31 is another perspective side view of the prototype collector of FIG. 30.

Figure 32:
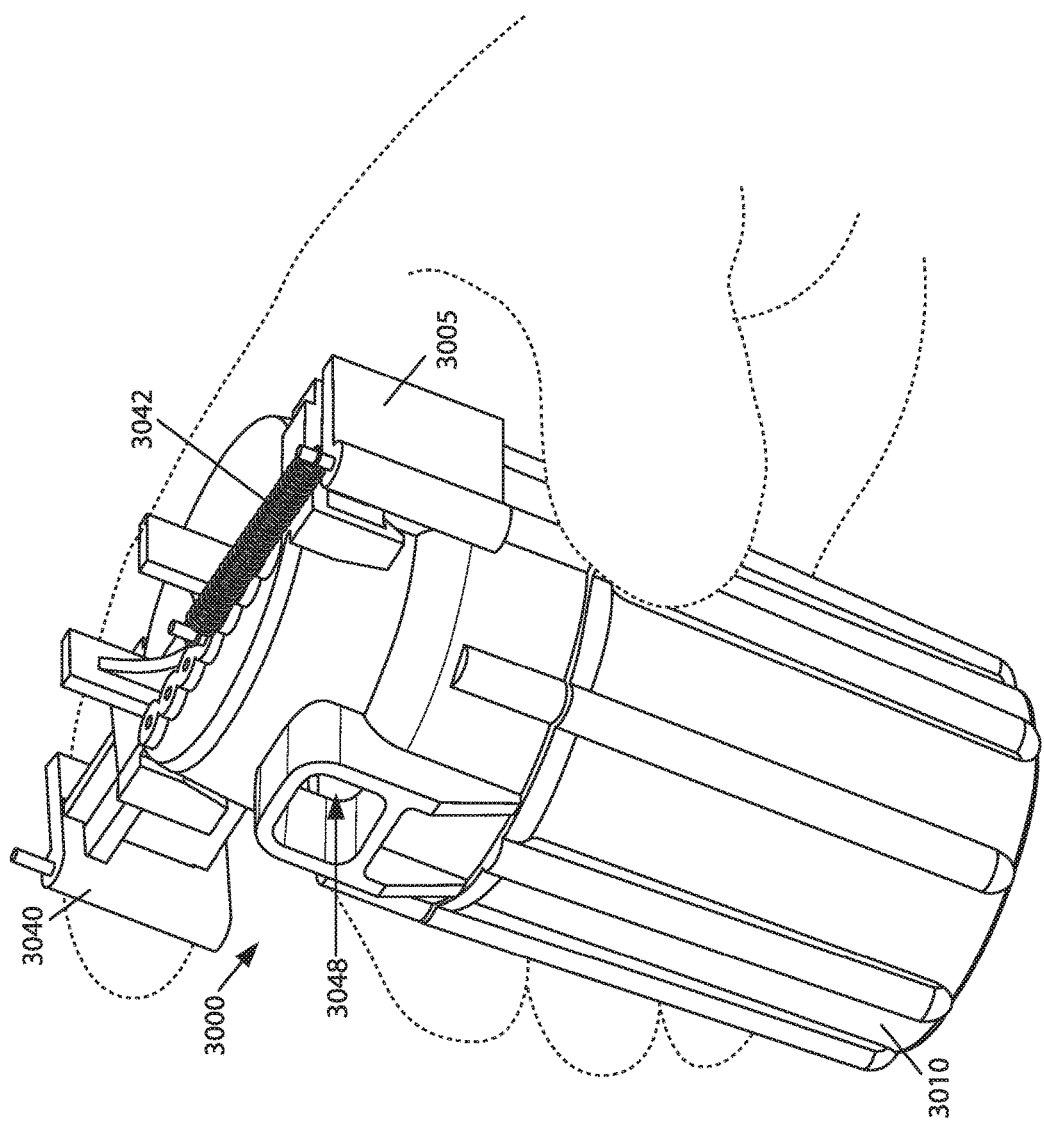

FIG. 32 is another perspective side view of the prototype collector of FIG. 30.

Figure 33A:
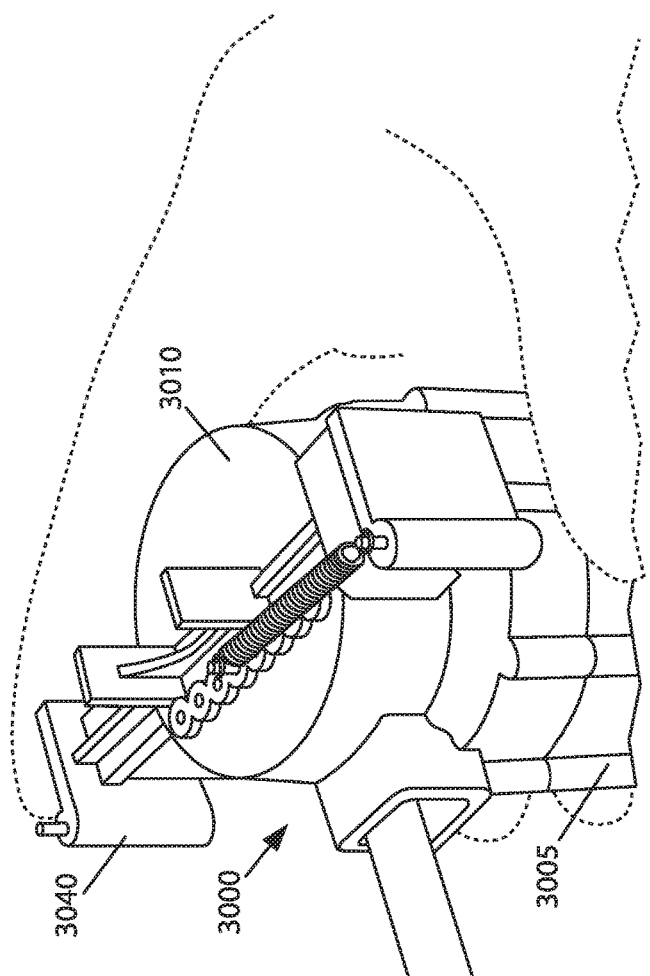

FIG. 33a is a perspective side view of the prototype collector of FIG. 30 with the tip of a rongeur inserted through the port thereof into the collector.

Figure 33B:
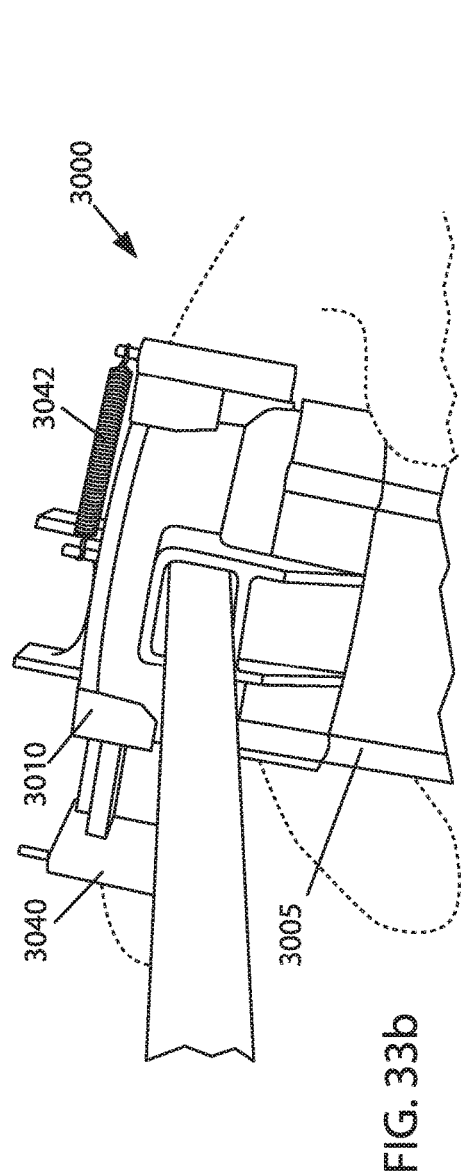

FIG. 33b is another perspective side view of the prototype collector of FIG. 30 with the tip of the rongeur inserted through the port thereof into the collector.

Figure 34A:
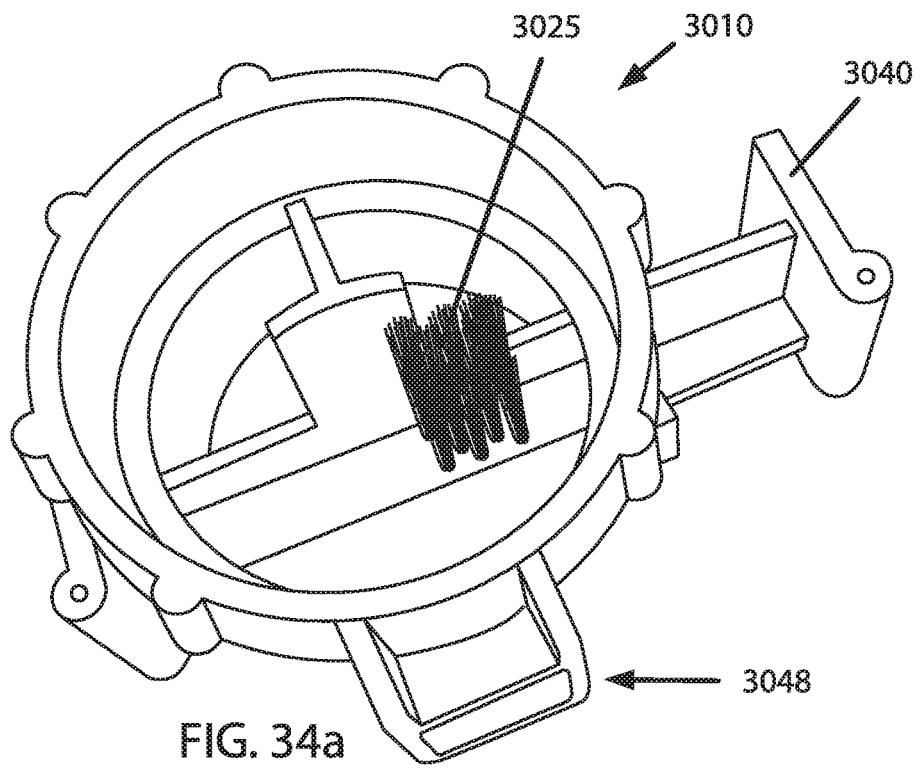

FIG. 34a is a perspective view of the underside of the cap of the prototype collector of FIG. 30, wherein the scraper attached to the slidable plunger for clearing material from the cutting area perhaps is best seen.

Figure 34B:
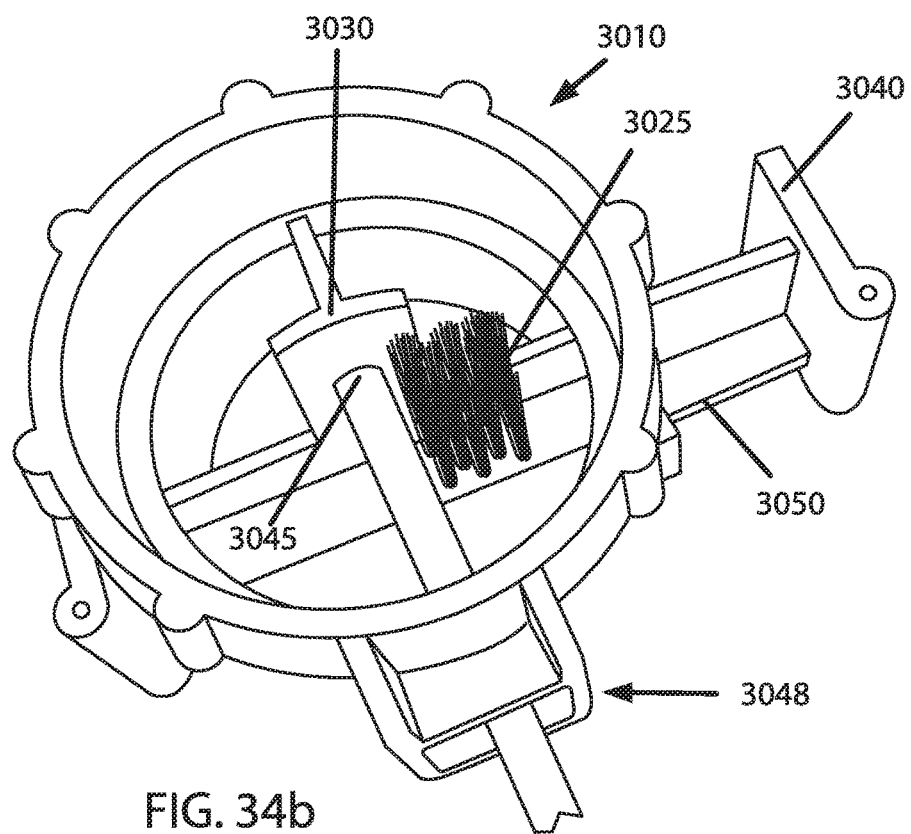

FIG. 34b is a perspective view of the underside of the cap of the prototype collector of FIG. 30, wherein the stop of the cap, against which the tip of the rongeur rests when fully inserted, is perhaps best seen.

DETAILED DESCRIPTION

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention in any claim of a patent issuing here from, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112(f), no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Additionally, as used herein, "cap" denotes "a lid configured to be attached to an object in covering relation to an interior containment space of the object".

As used herein, a "scraper" is a brush, a group of bristles, a protuberance, a barb, or a finger; and is sufficiently rigid so as to generally hold form when not engaged by the distal end of a kerrison rongeur and to generally dislodge bone found in a cutting area of a kerrison rongeur when moved into or through the cutting area. Preferably, a scraper also is sufficiently flexible and resilient so as to generally deflect and bend to some extent upon abutment by and engagement with the distal end of a kerrison rongeur. A scraper may be relatively hard or soft within this range. Furthermore, a scraper preferably comprises a bio-absorbable material in at least some embodiments of the invention. In this respect, a scraper may comprise a brush with bio-absorbable bristles which, if inserted into the body, are absorbed by the body.

Referring now to the drawings, one or more preferred embodiments of the present invention are next described. The following description of one or more preferred embodiments is merely exemplary in nature and is in no way intended to limit the invention, its implementations, or uses.

A First Embodiment

Accordingly, a perspective view of a collector 100 used to collect cut bone from a kerrison rongeur is shown in FIG. 2*a*. The collector 100 is in accordance with a first embodiment of the present invention and is illustrated in a generally vertical orientation in FIG. 2*a*. A perspective view of a sequence of steps for using the collector 100 in collecting bone from a kerrison rongeur is represented in FIG. 2*b*, in which figure the collector 100 is illustrated in a generally horizontal orientation.

As will be appreciated, the collector 100 is hand-held and comprises a container body 101 (shown in FIG. 2*a* and FIG. 2*b* to be a generally elongate body or tube that is cylindrical in shape), and having opposite, axially-aligned end caps 102,104. The container body 101 defines an interior containment space and comprises an opaque wall portion 103 and a transparent wall portion 105.

In use, the collector 100 is manually held at opposite ends in a generally horizontal position, as shown in FIG. 2*b*, in which it is positioned to receive the distal end 108 of a kerrison rongeur containing cut bone 110. The distal end 108 is received through an intake port opening 106 that is located in side wall portion 103 halfway in-between the opposite ends of the collector 100. In this respect, the collector 100 is held sideways and is said to be side-loaded.

Preferably in use, a scrub nurse, assisting technician, or similar person (hereinafter generally "assistant") moves or loads the collector 100 onto the distal end 108 of the kerrison rongeur when extended from the surgical site by the surgeon, who preferably maintains focus and attention on the surgical site and does not look away for purposes of aligning the distal end 108 with the intake port opening 106 (which alignment is the assistant's responsibility); it will be appreciated that the intake port opening 106 is maneuvered relative to and aligned with the distal end 108 by the assistant.

Upon receipt of the distal end 108 with the cut bone 110 through the opening 106 into the interior of the collector 100, the assistant depresses (pushes inwardly in direction of arrows A) on spring-loaded, axially-aligned end buttons 112,114 located on the opposite end caps 102,104 of the collector 100, respectively. In this respect, the buttons preferably are urged or biased by springs (not visible in FIG. 2*a* or 2*b*) in directions opposite to the arrows A in FIG. 2*a* so as to extend outwardly from the body 101 for grasping and holding of the collector 100 by the assistant during maneuvering of the collector onto the distal end 108 of the kerrison rongeur. This causes opposed interior scrapers 116,118 located in the interior of the collector 100 and connected to the end caps 102,104 to converge onto and cover the distal end 108 of the kerrison rongeur when received within the interior of the collector 100 through the port opening 106. This action—especially when performed multiple times—should serve to dislodge the bone 110 from the kerrison rongeur, resulting in the bone 110 either becoming lodged within the scrapers or falling onto an interior wall of the collector 100 defining at least in part the interior containment space. Moreover, the scrapers 116,118 optionally may be rotatable about a longitudinal axis L of the container body 101 by respective manual rotation of the end buttons 112, 114. The transparency of the wall portion 105 will enable the assistant to view whether the bone 110 has been collected yet from the kerrison rongeur, and to continue actuating the end buttons 112,114 either until the bone 110 has been collected or a reasonable number of attempts has been tried.

Once collected, the assistant removes (unloads) the collector 100 from the distal end 108 of the kerrison rongeur with the bone 110 remaining within the interior of the collector 100, either loosely retained therein or lodged within one of the opposed scrapers 116,118. Preferably the assistant then acknowledges to the surgeon the completion of the collection of the bone from kerrison rongeur, whereupon the surgeon returns the kerrison rongeur to the surgical site for continued cutting. This sequence continues until cutting by the surgeon is completed.

During the procedure, the bone 110 may be kept within the collector 100 until needed or may be removed as desired. The bone 110 preferably is harvested by removing each of the end caps 102,104 from the elongate body 101 of the collector 100. FIG. 2c is a perspective view of a scraper 118 of an end cap 114 of the collector 100 after bone has been collected from a kerrison rongeur and the end cap 114 has been detached from the body 101. In this respect, each of the end caps 112,114 preferably is received within an end of the elongate body 101 and retained thereby by a friction fit, for example, between the wall of the body 101 and a rubber or silicone seal 115; and/or a threaded engagement by screwing (not shown). Bone that is lodged within a scraper 116,118 of an end cap 102,104 can be removed by manually agitating the scraper 116,118 and pulling on the bone, with the scraper 116,118 extending over a sterile cloth, towel, pad, or table surface to catch the falling bone. Similarly, the bone within the body 101 of the collector 100 that is loose may be dumped onto a sterile cloth, towel, or pad, or directly onto a sterile surface of a table. The transparent portion 105 of the body 101 further may comprise a hinged or removable panel, by which the interior of the body 101 may be accessed for manual removal of any bone that may become stuck within the interior containment space of the body 101. The harvested bone then can be used during the procedure, such as for example, in an autograft procedure.

The materials from which the components of the collector are made may be any desired, suitable material for use in the foregoing procedure. For instance, a scraper may comprise metal or other rigid or semi-rigid material that is effective in dislodging bone from the distal end of the kerrison rongeur. It is further contemplated that one or more of the materials may be molded from, for example, an inert plastic material. Furthermore, the materials preferably are lightweight such that the collector is readily manipulated by hand. Furthermore, the collector may be disposable, in that the collector may be used during a single medical procedure for a patient and then discarded in accordance with applicable HAZMAT protocols. Alternatively, one or more components of the collector (including all of the components) are designed to and are able to be sterilized for reuse with another patient during another procedure.

A Second Embodiment

FIG. 3a is a perspective view of a collector 200 used to collect cut bone from a kerrison rongeur in accordance with a second embodiment of the present invention. The collector 200 is illustrated in a generally vertical orientation in FIG. 3a. A perspective view of the collector 200 representing a sequence of steps for using the collector 200 to collect bone from a kerrison rongeur is shown in FIG. 3b, wherein the collector 200 is illustrated in a generally horizontal orientation.

The collector 200 is hand-held and comprises a container body 201, shown to be generally cylindrical in shape. The container body 201 defines an interior containment space and includes a transparent sidewall portion 203 through which the interior of the container body 201 is visible.

The collector 200 further comprises a cap 205 that is attached to the container body 201. FIG. 3c is a top plan view of the cap 205 of the collector 200, and FIG. 3d is a side elevational view of the cap 205 of the collector 200.

The top of the cap 205 includes an intake port opening 213 centrally located in the top of the cap 205, perhaps as best shown in FIG. 3c. The top of the cap 205 includes a funnel-shaped surface 202 that is radially inclined toward the opening 213, as perhaps best shown in FIG. 3b. The cap 205 further includes a platform 207 that extends into the interior of the container body 201, as perhaps best shown in FIG. 3b. The platform 207 includes a stop 209 and scrapers 211. The scrapers 211—two of which are shown in the figures, but any number of which may be included—extend from the platform and are flexible and resilient, preferably sufficiently rigid or semi-rigid so as to hold form when not engaged by the distal end of a kerrison rongeur and deflecting and bending upon abutment by and engagement with the distal end of a kerrison rongeur. The scrapers 211 may be made from metal or other material, and it is contemplated that a scraper may be made of polypropylene.

It will be appreciated that the funnel-shaped top surface 202 of the cap 205 is designed to direct a distal end of a kerrison rongeur toward the opening 213 upon abutment therewith, and the stop 209 is intended to abut and physically preclude further advancement of the distal tip of the kerrison rongeur when received through the opening 213.

The cap 205 is freely rotatable relative to the container body 201, as indicated by the arrow R in FIG. 3b. Rotation—or twisting—of the cap 205 on the container body 201 is facilitated by external ribs 215 on the side of the cap 205 for manual grasping. Rotation of the cap 205 does not detach the cap 205 from the container body 201, which preferably is received and held within a mouth of the container body 201 in a frictional fit between the container body and a seal 217 of the cap 205. The cap 205 preferably is removable by pulling of the cap 205 off of the container body 201 with a reasonable amount of effort.

The stop 209 is located at a spacing relative to the opening 213 such that, upon receipt of the distal end of the kerrison rongeur and abutment thereof with the stop 209, the scrapers 211 extend over and cover the distal end of the kerrison rongeur proximate the cutting area in which cut bone would be found. Furthermore, rotation of the cap results in movement of the scrapers 211 around, about and through the cutting area of the distal end of the kerrison rongeur so as to dislodge and remove for collection any cut bone carried therein.

In this respect, the collector 200 is held horizontally generally as shown in FIG. 3b.

Preferably in use, an assistant moves or loads the collector 200 onto the distal end of a kerrison rongeur when extended from the surgical site by the surgeon, who preferably maintains focus and attention on the surgical site and does not look away for purposes of aligning the distal end with the intake port opening 213, which is generally located in the center of the cap 205. Alignment is the assistant's responsibility, and it will be appreciated that the intake port opening 213 is maneuvered relative to and aligned with the distal end of the kerrison rongeur by the assistant. The funnel-shaped surface 202 facilitates the alignment with and receipt of the distal tip within the opening 213.

Upon receipt of the distal end of the kerrison rongeur into the interior of the collector 200 and its abutment with the stop 209, the assistant twists (rotates in direction of arrow R) the cap 205 relative to the container body 201. This causes the scrapers 211 to engage and remove any cut bone carried by the kerrison rongeur, resulting in the bone either falling onto an interior wall of the container body 201 or becoming lodged within a scraper. Moreover, the transparency of the container body 201 will enable the assistant to view whether the bone has been collected yet from the kerrison rongeur, and to continue twisting the cap 205 on and relative to the container body 201 either until the bone has been collected or a reasonable number of rotations has occurred.

Once collected from the kerrison rongeur, the assistant removes (unloads) the collector 200 from the distal end of the kerrison rongeur with the bone remaining within the interior of the collector 200, either loosely retained therein or lodged within a scraper. Preferably the assistant then acknowledges to the surgeon the completion of the collection of the bone from kerrison rongeur, whereupon the surgeon returns the kerrison rongeur to the surgical site for continued cutting. This sequence continues until cutting by the surgeon is completed.

During the procedure, the bone may be kept within the collector 200 until needed or may be removed as desired. The bone preferably is harvested by removing the cap 205 from the container body 201. Bone that is lodged within a scraper can be removed by manually agitating the scraper and pulling on the bone so that the bone falls onto a sterile cloth, towel, pad, or table surface. The bone within the container body 201 that is loose may be dumped onto the sterile cloth, towel, or pad, or directly onto the sterile surface of the table. Bone within the container body 201 that is not loose may be manually removed. The harvested bone then can be used during the procedure, such as for example, in an autograft procedure.

The materials from which the components of the collector are made may be any desired, suitable material for use in the foregoing procedure. For instance, a scraper may comprise metal or other rigid or semi-rigid material that is effective in dislodging bone from the distal end of the kerrison rongeur. It is further contemplated that one or more of the materials may be molded from, for example, an inert plastic material. Furthermore, the materials preferably are lightweight such that the collector is readily manipulated by hand. Furthermore, the collector may be disposable, in that the collector may be used during a single medical procedure for a patient and then discarded. Alternatively, one or more components of the collector (including all of the components) are designed to and are able to be sterilized for reuse with another patient during another procedure.

A Third Embodiment

FIG. 4a is a perspective view illustrating a sequence of steps for using another collector 300 in accordance with a third embodiment of the present invention, wherein the collector 300 is illustrated in a generally horizontal orientation receiving the distal end of a kerrison rongeur. FIG. 4b is a top plan view of the collector 300 and distal tip of the kerrison rongeur of FIG. 4a. The collector 300 and use thereof is similar to collector 200 and its use, with the exception that a cap 305 of the collector includes a cut out 308 in the side thereof by which an assistant may better visualize alignment with and receipt of the distal end of a kerrison rongeur within the intake port opening in the cap 305, and with the further exception that the cap further does not include a funnel-shaped top surface.

A Fourth Embodiment

FIG. 5a a perspective view of a collector 400 used to collect cut bone from a kerrison rongeur for harvesting in accordance with another embodiment of the present invention, wherein the collector 400 is illustrated in a generally vertical orientation. FIG. 5b is a perspective view representative of a sequence of steps for using the collector 400 in collecting bone from a kerrison rongeur, wherein the collector 400 is illustrated in a generally horizontal orientation with the distal end of the kerrison rongeur being received within the collector 400.

The collector 400 is hand-held and comprises a container body 401, shown to be generally cylindrical in shape. The container body 401 defines an interior containment space and includes a transparent sidewall portion 403 through which the interior of the container body 401 is visible. The collector 400 further comprises a cap 405 that is attached to the container body 401. The cap 405 includes an interior ledge 411 that defines an intake port opening 413 through which the distal end of a kerrison rongeur is received. The cap 405 further includes a guide member 417 that projects from the ledge 411 and that is shaped and contoured for receiving and guiding therein a portion of the distal end of the kerrison rongeur. The guide member 417 preferably includes a U-shape configuration, as shown. An saddle member 419 extends from a bottom 409 of the container body 401 and, in conjunction with the guide member 417, assists in aligning the distal end of the kerrison rongeur for collection of bone, as shown in FIG. 5b. The saddle member 419 preferably includes a C-shape configuration, as shown.

A scraper 421 is provided proximate the bottom 409 of the container body 401 and extends toward the saddle member 419 into the cutting area of the distal end of a kerrison rongeur when aligned by the saddle member 419. The scraper 421 is secured to a base 423 that extends from the side wall 403 of the container body 401 in abutment with the bottom 409 of the container body 401. Further in this regard, the bottom 409 serves as a stop for the distal end of the kerrison rongeur.

The cap 405 is freely rotatable relative to the container body 401, as indicated by the arrows R in FIG. 5b. Rotation—or twisting—of the cap 405 on the container body 401 is facilitated by external ribs 416 on the side of the cap 405 for manual grasping. Rotation of the cap 405 does not detach the cap 405 from the container body 401, which preferably is received and held within a mouth of the container body 401 in a frictional fit between the container body and a seal (now shown, but similar to seal 217 found in collector 200). The cap 405 preferably is removable by pulling of the cap 405 off of the container body 401 with a reasonable amount of effort.

The scraper 421 is located at a spacing relative to the saddle member 419 such that, upon receipt of the distal end of the kerrison rongeur and abutment thereof with the bottom 409 serving as a stop, the scraper 411 extends over and covers the distal end of the kerrison rongeur proximate the cutting area thereof in which cut bone would be found. Furthermore, rotation of the container body 401 relative to the cap 405 results in movement of the scraper 421 around, about and through the cutting area of the distal end of the kerrison rongeur so as to dislodge and remove for collection any cut bone carried therein. It will further be appreciated that the saddle member 419 also rotates with the container body 401, whereas the guide member 417 is an integral molded part of—and remains fixed relative to—the cap 405.

It will further be noted that the cap 405 defines an inner surface 430 that, when the collector is positioned for receiving the distal end of the kerrison rongeur, as shown in FIG. 5*b*, the inner surface 430 will form a flange that catches bone that may fall from the kerrison rongeur while attempting to receiving the distal end of the kerrison rongeur within the guide member 417 and through the intake opening 413.

Preferably in use, an assistant moves or loads the collector 400 onto the distal end of a kerrison rongeur when extended from the surgical site by the surgeon, who preferably maintains focus and attention on the surgical site and does not look away for purposes of aligning the distal end with the intake port opening 413, which is generally located in the center of the cap 405. Alignment is the assistant's responsibility, and it will be appreciated that the intake port opening 413 is maneuvered relative to and aligned with the distal end of the kerrison rongeur by the assistant. The guide member 417 further aids the assistant in positioning of the distal end of the kerrison rongeur within the saddle member 419 after being inserted through the opening 413.

Upon receipt of the distal end of the kerrison rongeur into the interior of the collector 400 and its abutment with the bottom 409 serving as a stop, the assistant twists (rotates back and forth in the directions of arrows R) the container body 401 relative to the cap 405. This causes the scraper 421 to engage and remove any cut bone carried by the kerrison rongeur, resulting in the bone either falling onto an interior wall of the container body 401 or becoming lodged within the bristles of the scraper 421. Moreover, the transparency of the side wall 403 container body 401 enables the assistant to view whether the bone has been collected yet from the kerrison rongeur, and to continue twisting the container body 401 relative to the cap 405 back and forth either until the bone has been collected or a reasonable number of attempts have been made by the assistant.

Once collected from the kerrison rongeur, the assistant removes (unloads) the collector 400 from the distal end of the kerrison rongeur with the bone remaining within the interior of the collector 400, either loosely retained therein or lodged within the bristles. Preferably the assistant then acknowledges to the surgeon the completion of the collection of the bone from kerrison rongeur, whereupon the surgeon returns the kerrison rongeur to the surgical site for continued cutting without taking focus away from the surgical site. This sequence continues until cutting by the surgeon is completed.

During the procedure, the bone may be kept within the collector 400 until needed or may be removed as desired. The bone preferably is harvested by removing the cap 405 from the container body 401. Bone that is lodged within a scraper can be removed by manually agitating the bristles and pulling on the bone so that the bone falls onto a sterile cloth, towel, pad, or table surface. The bone within the container body 401 that is loose may be dumped onto the sterile cloth, towel, or pad, or directly onto the sterile surface of the table. Bone within the container body 401 that is not loose may be manually removed by hand or with an instrument. The harvested bone then can be used during the procedure, such as for example, in an autograft procedure.

The materials from which the components of the collector are made may be any desired, suitable material for use in the foregoing procedure. For instance, a scraper may comprise metal or other rigid or semi-rigid material that is effective in dislodging bone from the distal end of the kerrison rongeur. It is further contemplated that one or more of the materials may be molded from, for example, an inert plastic material. Furthermore, the materials preferably are lightweight such that the collector is readily manipulated by hand. Furthermore, the collector may be disposable, in that the collector may be used during a single medical procedure for a patient and then discarded. Alternatively, one or more components of the collector (including all of the components) are designed to and are able to be sterilized for reuse with another patient during another procedure.

FIG. 5*c* is a side elevational view of an alternative collector 400' generally similar to the collector 400, but in which the height of the collector 400' is less than the height of the collector 400 and, thus, the collector 400' has a smaller profile.

A Fifth Embodiment

FIG. 6*a* is a perspective view of a collector 500 used to collect cut bone from a kerrison rongeur for harvesting in accordance with another embodiment of the present invention, wherein the collector 500 is illustrated in a generally horizontal orientation. FIG. 6*b* is a side elevational view of the collector 500.

The collector 500 includes a container body 501 that is box-shaped with generally rectangular sides and a cap 505 with generally rectangular sides. The container body 501 defines an interior containment space and preferably includes transparent side walls 503. The container body 501 is utilized to store collected bone. The cap 505 includes a stop comprising a wall 519 that extends between opposed interior side surfaces of the cap 505 and divides passage through the cap to the interior of the container body 501 into two side passages 508 around opposite sides of the wall 519. Scrapers 521 are located in front of the wall and extend from one of the interior side surfaces of the cap 505 from to which the wall 519 connects.

Preferably in use, an assistant moves or loads the collector 500 onto the distal end of a kerrison rongeur when extended from the surgical site by the surgeon, who preferably maintains focus and attention on the surgical site and does not look away for purposes of aligning the distal end of the kerrison rongeur with the opening in the cap 505. Alignment is the assistant's responsibility, and it will be appreciated that the collector 500 is maneuvered relative to and aligned with the distal end of the kerrison rongeur by the assistant such that the distal end of the kerrison rongeur, when received within the cap 505, will come into abutment with the wall 519 and cease further advancement within the cap 505 toward the container body 501. The spacing of the wall 519 to the scrapers 521 is such that the scrapers will pass through the cutting area of the distal end of the kerrison rongeur when the collector 500 is moved back and forth in lateral directions relative to the longitudinal extent of the kerrison rongeur. Furthermore, the wall 519 may be maintained in abutment with the tip of the kerrison rongeur during such back and forth movement for proper alignment of the scarpers 521 relative to the cutting area of the kerrison rongeur, thereby facilitating dislodgment of cut bone found in the cutting area by the scrapers 521. Such back and forth movement is facilitated by longitudinally protruding ribs 515 on the cap 505, which enable better grasping by hand of the cap 505. Additionally, one or more ribs 515—such as the middle pair of ribs shown in FIGS. 6*a* and 6*b*, for example— may be used for sighting by the assistant during loading of the distal end of the kerrison rongeur, as represented by the direction and alignment of arrow A relative to the middle pair of ribs seen in FIG. 6b.

Once collected from the kerrison rongeur, the assistant removes (unloads) the collector 500 from the distal end of the kerrison rongeur with the bone remaining within the interior of the cap 505, either loosely retained therein or lodged within the bristles. Tilting of the collector 500 to a vertical orientation and light shaking of the collector 500 should cause any loose bone collected from the kerrison rongeur to fall through one of the side passages into the container body 501 where the bone yield can be viewed through the transparent walls 503.

Preferably the assistant acknowledges to the surgeon the completion of the collection of the bone from kerrison rongeur, whereupon the surgeon returns the kerrison rongeur to the surgical site for continued cutting without taking focus away from the surgical site. This sequence continues until cutting by the surgeon is completed.

During the procedure, the bone may be kept within the container body 501 of the collector 500 until needed or may be removed as desired. The bone preferably is harvested by removing the cap 505 from the container body 501. Bone that is lodged within any bristles of the scrapers 521 can be removed by manually agitating the bristles and pulling on the bone so that the bone falls onto a sterile cloth, towel, pad, or table surface. The bone within the container body 501 that is loose may be dumped onto the sterile cloth, towel, or pad, or directly onto the sterile surface of the table. Bone within the container body 501 that is not loose may be manually removed by hand or with an instrument. The harvested bone then can be used during the procedure, such as for example, in an autograft procedure.

The materials from which the components of the collector are made may be any desired, suitable material for use in the foregoing procedure. For instance, a scraper may comprise metal or other rigid or semi-rigid material that is effective in dislodging bone from the distal end of the kerrison rongeur. It is further contemplated that one or more of the materials may be molded from, for example, an inert plastic material. Furthermore, the materials preferably are lightweight such that the collector is readily manipulated by hand. Furthermore, the collector may be disposable, in that the collector may be used during a single medical procedure for a patient and then discarded. Alternatively, one or more components of the collector (including all of the components) are designed to and are able to be sterilized for reuse with another patient during another procedure.

A Sixth Embodiment

FIG. 7a is a perspective view of a collector 600 used to collect cut bone from a kerrison rongeur in accordance with another embodiment of the present invention, wherein the collector 600 is illustrated in a generally horizontal orientation. Each of FIGS. 7b, 7c is a respective side elevational view of the collector 600. The collector 600 is similar in construction and use as the collector 500 discussed above with reference to FIGS. 6a and 6b. A primary difference over the collector 500, however, is that the wall 521 is replaced with a depressible button 621. The button 621 preferably is spring-loaded and biased into an extended position, shown in FIG. 7a in solid line and additionally shown in FIG. 7b, in which extended position passage through the cap 605 to an interior containment space of the container body 601 is not blocked. Upon being fully depressed, the button extends into and blocks passage through the cap 605, as shown in phantom in FIG. 7a. When in the depressed position, the button serves as a stop in same manner as wall 519 in collector 500, described above.

A Seventh Embodiment

FIG. 8a is a perspective view of a collector 700 used to collect cut bone from a kerrison rongeur for harvesting in accordance with another embodiment of the present invention, wherein the collector 700 is illustrated in a generally horizontal orientation. The collector 700 is similar in construction and use as the collector 600 discussed above with reference to FIG. 7a, FIG. 7b, and FIG. 7c. A primary difference over the collector 600, however, is that the cap includes a ramp 704 that assists in guiding the tip of the end portion of a kerrison rongeur into proper position within the cap. The height of the passage is also less than that of the height of the passage through cap 605, and the length of travel when depressing the button is consequently less as well.

An Eighth Embodiment

FIG. 9a is a perspective view of a collector 800 used to collect cut bone from a kerrison rongeur for harvesting in accordance with another embodiment of the present invention, wherein the collector 800 is illustrated in a generally horizontal orientation. FIG. 9b is a perspective view of part of a release mechanism 840 of the collector 800, and FIG. 9c is a schematic illustration representing the arrangement and operation of the release mechanism 840 relative to the scrapers 821 and cap 805 of the collector 800.

The collector 800 includes a release mechanism 840 having a button 823 connected by an arm 842 to a wall 843. The wall 843 defines a release opening 844 therein. The release mechanism 840 is contained within the cap 805 and includes a spring 845 that biases the release mechanism 840 into a closed configuration, wherein bone collected within intake port 813 using scrapers 821 is blocked from access to an interior containment space of the container body 801. When the button 823 is depressed against the biasing of the spring 845 in the direction of arrow A, the wall 843 moves (slides) so as to align the release opening 844 with the intake port opening 813 thereby permitting the collected bone to pass to the interior of the container body 801. When in the closed configuration, the wall 843 serves as a stop for the distal end of a kerrison rongeur, in which position the scrapers 821 pass through the cutting area when the cap 805 is rotated about its longitudinal axis relative to the kerrison rongeur.

Additional Embodiments Utilizing Suction

Additional collectors used to collect cut bone from a kerrison rongeur for harvesting in accordance with still yet more embodiments of the present invention embodiments are disclosed with reference to FIGS. 10a through 19c. Each of these additional embodiments utilizes suction and includes a suction port for attachment thereto of a suction hose or tube. The hose or tube in turn is connected to a suction source, such as those commonly found in operating rooms.

A collector 900 in accordance with a first such embodiment is shown in FIGS. 10a and 10b, wherein a perspective view of the collector 900 used to collect cut bone from a kerrison rongeur for harvesting is illustrated in a generally vertical orientation and includes a suction tube 950 attached to a suction port 952 located on the cap 905 of the collector 900. FIG. 10*b* is a side plan view of the collector 900 that perhaps better shows in a close-up, cross-sectional view, the configuration of the intake port 913 of the collector 900 within which a distal tip of a kerrison rongeur is received. In accordance with this embodiment, the intake port includes one or more scrapers located within the interior thereof. Additionally, the intake port 913 itself forms a "hawk bill" scraping tip. The scrapers and scraping tip are used to dislodge and scrape bone from the kerrison rongeur, with the suction applied through the suction tube drawing into the collector the dislodged and scraped bone. The bone is caught and retained within an interior containment space of the container body 901 for later harvesting and use.

FIG. 11*a* is a perspective view of a collector 1000 used to collect cut bone from a kerrison rongeur for harvesting in accordance with yet another embodiment of the present invention, wherein the collector 1000 is illustrated in a generally vertical orientation and includes a suction tube 1050 attached to a suction port 1052 located on the cap 1005 of the collector 1000. FIG. 11*b* is a side plan view of the collector 1000.

Unlike collector 900, the cap 1005 of collector 1000 forms a long, ergonomic handle 1075 for gripping where the suction port 1052 is located. Like collector 900, the intake opening 1013 of collector 1000 is formed in the cap 1005 and includes scrapers 1021 located within the interior thereof, as seen in FIG. 11*a*.

FIG. 12*a* is a side plan view, in cross-section, of a collector 1100 used to collect cut bone from a kerrison rongeur in accordance with yet another embodiment of the present invention, wherein the collector 1100 is illustrated in a generally vertical orientation and includes a suction tube 1150 attached to a suction port 1152 located on the cap 1105. As shown in FIG. 12*a*, the collector 1100 includes multiple interior scrapers 1121 extending from the cap 1105 downwardly within the interior thereof for dislodging bone from the distal end of a kerrison rongeur.

FIG. 12*b* is a side plan view in cross-section of another collector 1200 similar to the collector 1100 of FIG. 12*a*, and differing only in that a single interior scraper 1221 is provided rather than a plurality of scrapers.

FIG. 12*c* is a perspective view in cross-section of a portion of the collector 1100 of FIG. 12*a* illustrating a porous screen mesh or screen 1190 for filtering of outflow from the collector 1100 through the suction tube 1150 so that precious bone is not inadvertently suctioned away from the collector 1100. Indeed, a screen is preferred as the collector is most likely will be accidentally tipped over onto its side at some point during its use such that bone would be suctioned away if not for the screen.

FIG. 13*a* is a perspective view of a collector 1300 used to collect cut bone from a kerrison rongeur for harvesting in accordance with yet another embodiment of the present invention, wherein the collector 1300 is illustrated in a generally vertical orientation. FIG. 13*b* is another perspective view of an opposite side of the collector 1300 as seen in FIG. 13*a*. The collector 1300 includes a suction tube 1350 attached to a suction port 1352 located at a distal end of a handle 1375 that, itself, is located proximate the bottom of the collector 1300. An airflow channel 1377 is defined within and extends through the interior of the handle 1375 between the suction port 1313 and an interior containment space of the container body 1301 (which is represented in phantom in FIGS. 13*a* and 13*b*). As shown in FIGS. 13*a* and 13*b*, the handle 1375 and suction port are part of the cap 1305, which is removably attached to the container body 1301. Intake port 1313 is also part of the cap 1305.

FIG. 14*a* is a perspective view of a collector 1400 used to collect cut bone from a kerrison rongeur in accordance with yet another embodiment of the present invention, wherein the collector 1400 is illustrated in a generally vertical orientation. FIG. 14*b* is a perspective view illustrating a use of the collector 1400 in collecting bone from a kerrison rongeur for harvesting, wherein the collector 1400 is illustrated in a generally horizontal orientation with the distal end of the kerrison rongeur about to be received through an intake port 1413 of the collector 1400 that is located on the top of the cap 1405 of the collector 1400.

FIG. 15*a* is a perspective view of a collector 1500 used to collect cut bone from a kerrison rongeur in accordance with yet another embodiment of the present invention, wherein the collector 1500 is illustrated in a generally vertical orientation. FIG. 15*b* is another perspective view of an opposite side of the collector 1500 as seen in FIG. 15*a*, wherein an intake port 1513 of the collector 1500 is better seen. The intake port 1513 is located on a side of the cap 1505 of the collector 1500.

FIG. 16*a* is a perspective view of a collector 1600 used to collect cut bone from a kerrison rongeur in accordance with yet another embodiment of the present invention, wherein the collector 1600 is illustrated in a generally vertical orientation. FIG. 16*b* is another perspective view of an opposite side of the collector 1600 as seen in FIG. 16*a*, wherein an intake port 1613 of the collector 1600 is better seen.

Figure 1A:
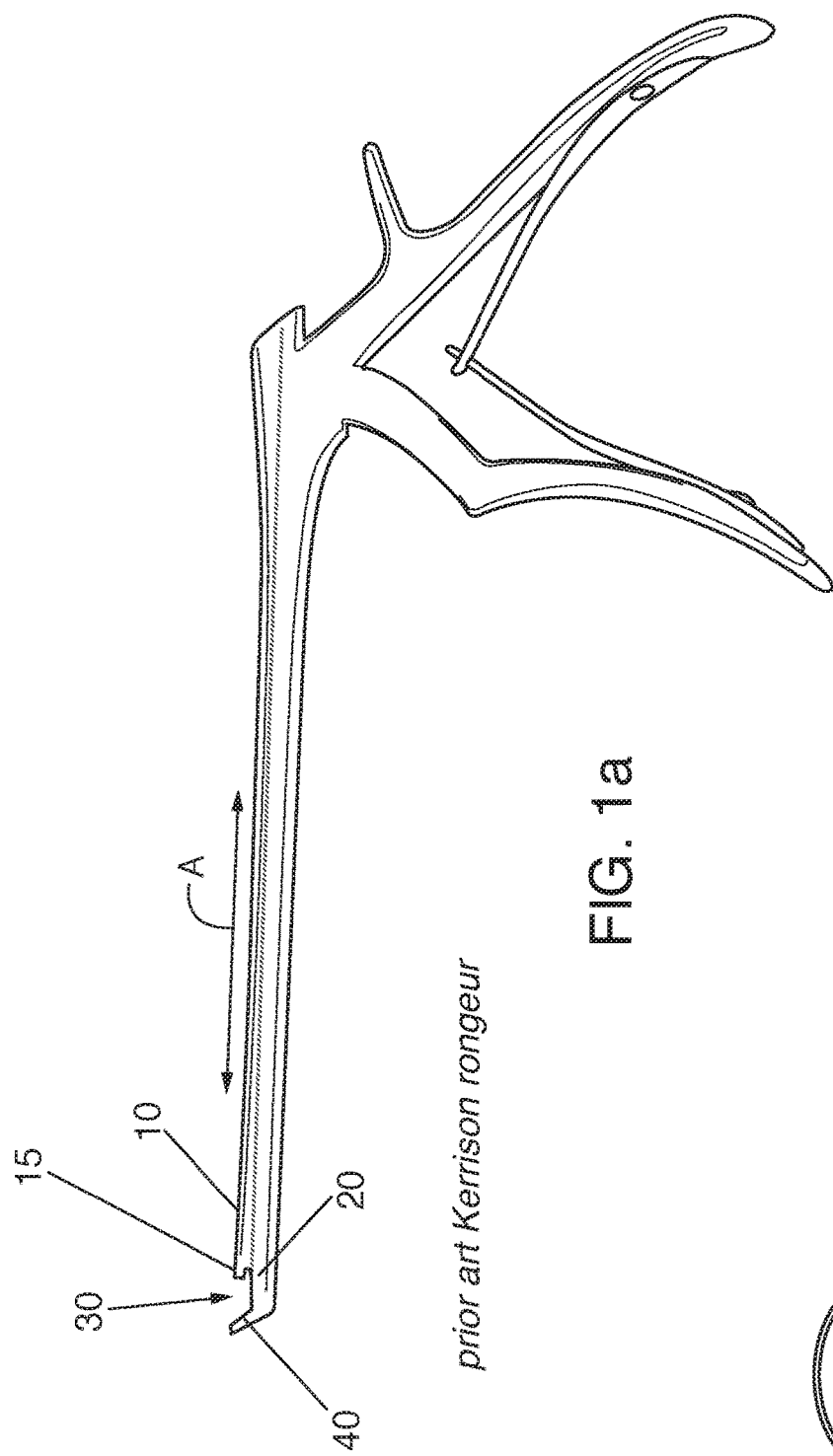
FIG. 1a is a side elevational view of an exemplary prior art kerrison rongeur.
Figure 1B:
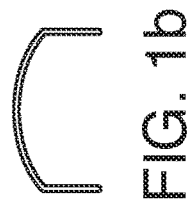
Figure 17A:
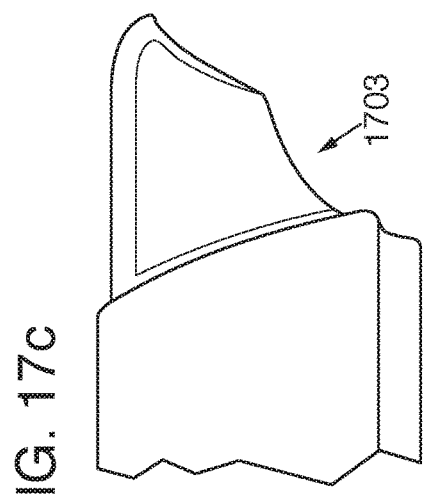

FIG. 17*a* illustrates, in a cross-sectional view, a profile of an intake port 1701 for a collector in accordance with various embodiments of the present invention, which intake port has a rounded, angled tip.

Figure 17B:
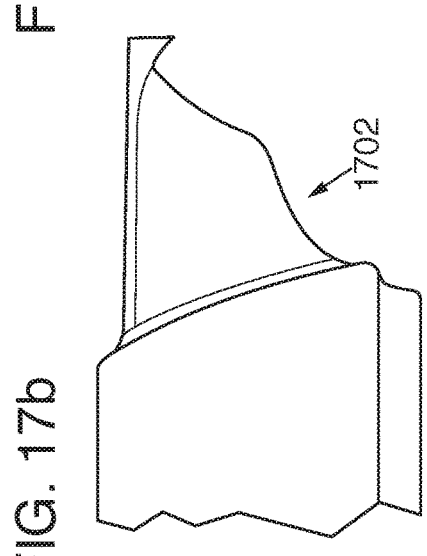

FIG. 17*b* illustrates, in a cross-sectional view, a profile of an intake port 1702 for a collector in accordance with various embodiments of the present invention, which intake port has a rounded, angled "hawk bill" scraping tip.

Figure 17C:
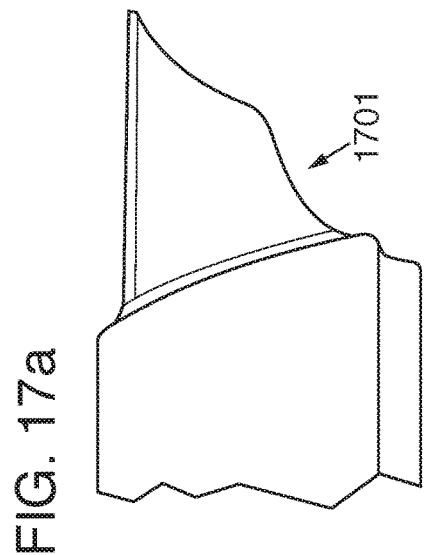

FIG. 17*c* illustrates, in a cross-sectional view, a profile of an intake port 1703 for a collector in accordance with various embodiments of the present invention, which intake port has a rounded, angled round hawk bill scraping tip.

Figure 17D:
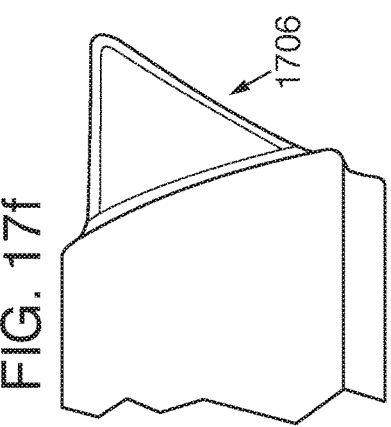

FIG. 17*d* illustrates, in a cross-sectional view, a profile of an intake port 1704 for a collector in accordance with various embodiments of the present invention, which intake port has a rounded, rectilinear tip.

Figure 17E:
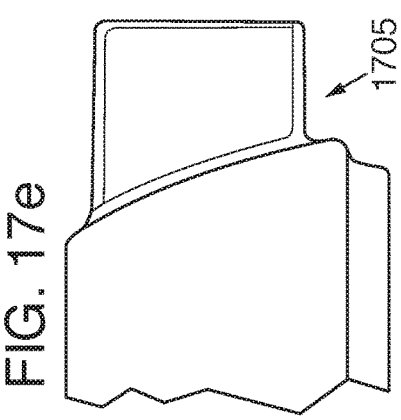

FIG. 17*e* illustrates, in a cross-sectional view, a profile of an intake port 1705 for a collector in accordance with various embodiments of the present invention, which intake port has a rectilinear tip.

Figure 17F:
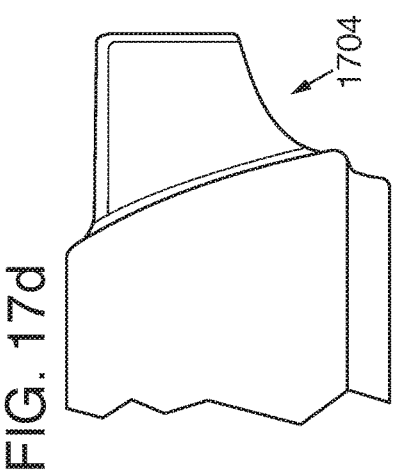

FIG. 17*f* illustrates, in a cross-sectional view, a profile of an intake port 1706 for a collector in accordance with various embodiments of the present invention, which intake port has an angled tip.

FIG. 18*a* illustrates in plan view an opening of an intake port 1801 for a collector in accordance with various embodiments of the present invention, which intake port includes multiple sets of bristle scrapers mounted on a top and sides of the port.

FIG. 18*b* illustrates in plan view an opening of an intake port 1802 for a collector in accordance with various embodiments of the present invention, which intake port includes side scrapers combined with one large top scraper.

FIG. 18*c* illustrates in plan view an opening of an intake port 1803 for a collector in accordance with various embodiments of the present invention, which intake port includes a single large top mounted scraper that scraps both sides and top simultaneously, and which port has a narrowed entrance to improve scraping efficiency upon insertion of a kerrison rongeur.

FIG. 19a illustrates in plan view a generally oval (preferably circular) intake port 1901 of for a collector in accordance with various embodiments of the present invention, which intake port includes top and side mounted scrapers.

FIG. 19b illustrates in plan view a generally oval (preferably circular) intake port 1902 for a collector in accordance various embodiments of the present invention, which intake port includes multiple top scrapers combined with side scrapers.

FIG. 19c illustrates in plan view a generally oval (preferably circular) intake port 1903 for a collector in accordance with various embodiments of the present invention, which intake port includes a single, top mounted scraper.

More Embodiments and Prototypes

Still another collector in accordance with an embodiment of the present invention is shown in a perspective view in FIG. 20. As shown therein, the intake port 2013 comprises a squeezable and springy material capable of being squeezed by hand. When the distal end of a kerrison rongeur is received within the intake port 2013, the intake port is manually squeezed such that scrapers located within the intake port 2013 engage and dislodge any cut bone found within the cutting area of the kerrison rongeur. The locations, types, and configurations of the scrapers may be in accordance with the disclosures of scrapers found hereinabove.

FIG. 21a illustrates a table listing values of properties giving rise to some possible variations between some embodiments of the invention, and FIG. 21b illustrates a table listing some possible combinations of some of the elements of the table of FIG. 21a. In this respect, the first column of the table of FIG. 21a lists elements that maybe used in one or more embodiments. The listed elements include a brush; a soft wiper (i.e., soft scraper); a hard wiper (i.e., hard scraper); pressure (air); and suction. Each of these elements represents a way of removing or dislodging cut matter from a tip of a rongeur. The second column lists paths of movement of the tip of the rongeur relative to the element for the brush and different wipers. The third column lists possible orientation to the path.

Exemplary combinations of some of these elements, including the brush and wipers, are set forth in FIG. 21b. FIGS. 22a through 22g are perspective views of tips and scrapers showing various paths and orientations.

In particular, FIG. 22a shows scraper 2202, rongeur 2204 with cutting area 2206, and a path of movement of the scraper 2202 relative to the rongeur 2204 and cutting area 2206; FIG. 22b shows scraper 2208, rongeur 2210 with cutting area 22012, and a path of movement of the scraper 2208 relative to the rongeur 2210 and cutting area 2212; FIG. 22c shows scraper 2214, rongeur 2216 with cutting area 2218, and a path of movement of the scraper 2214 relative to the rongeur 2216 and cutting area 2218; FIG. 22d shows scraper 2220, rongeur 2222 with cutting area 2224, and a path of movement of the scraper 2220 relative to the rongeur 2222 and cutting area 2224; FIG. 22e shows a scraper in the form of a wiper 2226, rongeur 2228 with cutting area 2230, and a path of movement of the wiper 2226 relative to the rongeur 2228 and cutting area 2230; FIG. 22f shows a scraper in the form of a wiper 2232, rongeur 2234 with cutting area 2236, and a path of movement of the wiper 2232 relative to the rongeur 2234 and cutting area 2236; and FIG. 22g shows a scraper in the form of a wiper 2238, rongeur 2240 with cutting area 2242, and a path of movement of the wiper 2238 relative to the rongeur 2240 and cutting area 2242.

A perspective view of a collector 2300 in accordance with yet another embodiment of the invention is illustrated in FIG. 23.

A perspective view of a collector 2400 in accordance with yet another embodiment of the invention—and structurally similar in design to the embodiment of FIG. 23—is illustrated in FIGS. 24a-24f, wherein: FIG. 24a is a top view of the cap of the collector 2400; FIG. 24b is a side elevational view of the collector 2400; FIG. 24c is another side elevational view of the collector 2400; FIG. 24d is a top perspective side view of the collector 2400; FIG. 24e is a bottom perspective side view of the collector 2400; and FIG. 24f is a perspective view of the scraper of the collector 2400 located under and attached to the cap, as seen through the opening in the cap in FIGS. 24c and 24e.

A perspective view of a collector 2500 in accordance with yet another embodiment of the invention is illustrated in FIGS. 25a-25f. A portion 2580 of the end of a kerrison rongeur including the tip also is illustrated relative to the container 2500 in FIGS. 25b-25f.

A perspective view of two collectors 2600,2650 each in accordance with another respective embodiment of the invention are illustrated in FIGS. 26a-24f. The two collectors 2600,2650 are structurally the same with the exception that brush 2610 of collector 2600 comprises bristles of the same length, whereas brush 2660 of collector 2650 has varying length bristles. In particular, FIG. 26a is a side-by-side elevational view of the tops of the collectors 2600,2650 looking through the ports (wide side openings) in the caps thereof at the brushes 2610,2660, where the varying length bristles of brush 2660 can be seen. FIG. 26b is a perspective view of the caps of the collectors 2600,2650 after the caps have been unscrewed from the containers and placed upside down on a surface to expose views of the brushes 2610, 2660. As perhaps best shown in FIG. 26b, the brushes are secured to a generally semicircular area of the underside of the respective caps. Continuing with reference to collectors 2600,2650, FIG. 26c is a side-by-side top perspective view of these collectors, and FIG. 26d is a side elevational view of collector 2650 being held with a left hand. The varying length of the bristles of brush 2660 also are seen in FIG. 26d as well.

Figure 28:
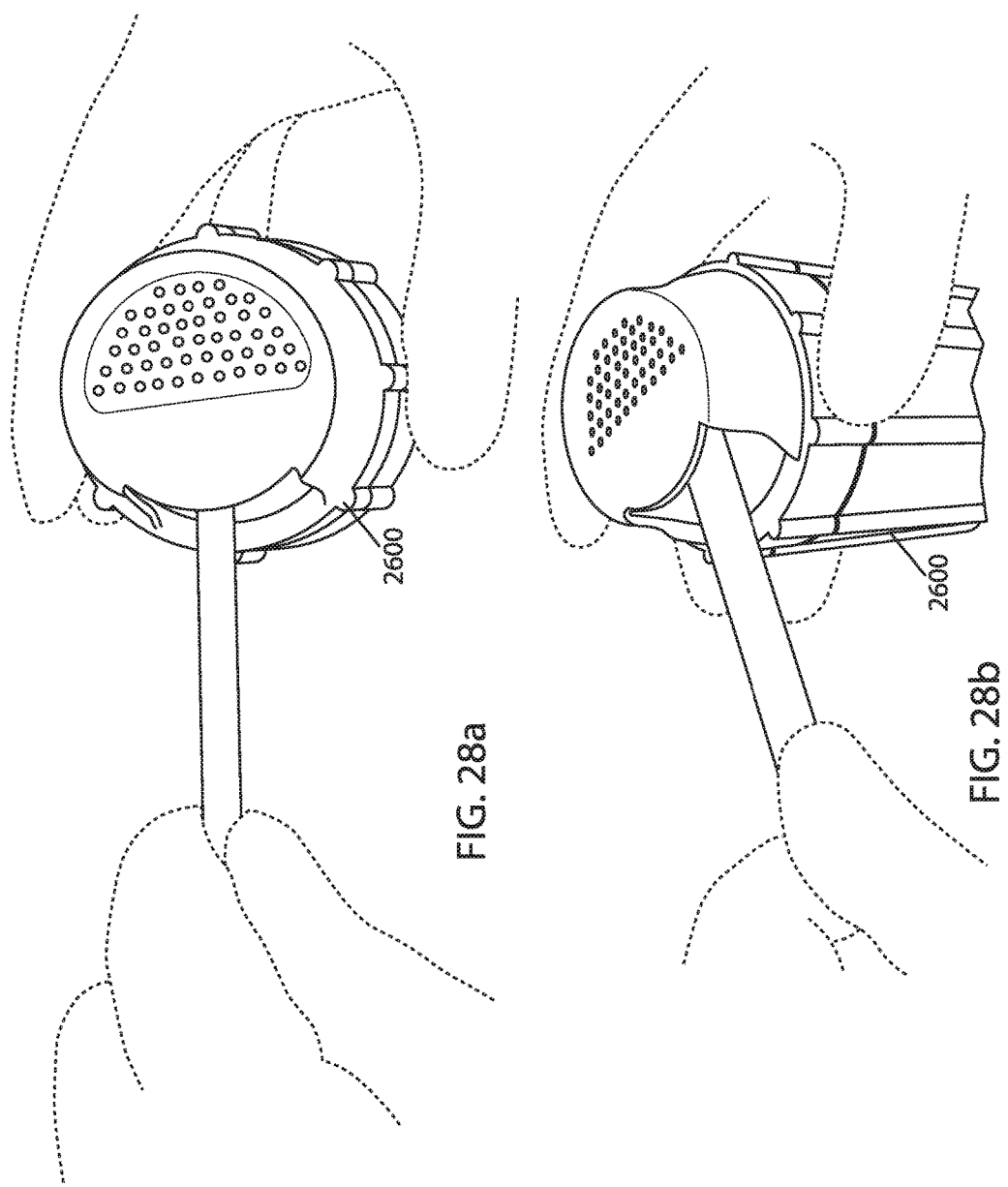

FIGS. 27-28b demonstrate insertion of the tip of a kerrison rongeur through the port and into the interior of the cap of the collector 2600 in engagement with the brush 2610. Specifically, FIG. 27 shows movement of the tip in the direction of arrow A so as to extend through the port; and FIGS. 28a and 28b each shows the tip being receive within the cap of the collector 2600 in engagement with the brush 2610.

A perspective view of a collector 2900 in accordance with yet another embodiment of the invention is illustrated in FIG. 29 and comprises a container 2905 and cap 2910. The cap includes a slidable plunger that is spring-biased into an open position by spring 2942. A scraper is located on the plunger inside the cap 2910 and, when the plunger is moved (slides) into the closed position by pressing on tab 2940 with a finger or thumb, the scraper (not shown) moves across the cutting area of a rongeur tip that has been inserted through port 2948 so as to dislodge and clear matter carried on the rongeur in the cutting area.

FIGS. 30-34b show a prototype collector 3000 as represented by collector 2900 of FIG. 29. In particular, FIG. 30 shows the collector 3000 held in a person's left hand with thumb on the tab 3040 of the plunger. An alternative method of holding the collector is with the right hand, as demonstrated in FIGS. 31 and 32.

The plunger is biased by spring 3042 into an open position. FIG. 34a shows the plunger 3050 in an open position. The spring is attached and secured at one end by a pin to the plunger, and at the other end by a pin to the main body of the cap 3010. In order to adjust the spring force, the pin can be placed in one of a plurality of holes formed in the cap 3010 as perhaps best seen in FIG. 30 and illustrated in representative collector 2900 of FIG. 29. The cap 3010 includes a port 3048 physically configured to receive the tip of a kerrison rongeur there through, as seen in FIGS. 33a and 33b.

When inserted through the port 3048, the distal end 3045 of the tip of the rongeur contacts a stop 3030, which is best seen in FIG. 34b. Indeed, in FIG. 34b the tip is shown having been inserted through port 3048 of cap 3010 and into abutment with stop 3030, whereat movement of the plunger by pressing on tab 3040 will force the scraper (in the form of a brush 3025) directly through the cutting area of the tip, thereby dislodging matter in the cutting area.

In accordance with preferred embodiments of the present invention, a patient advantageously is afforded his or her own bone for the fusion when a collector is used to harvest bone cut from the patient using a kerrison rongeur. For example, Lamina chips are clinically proven to have both osteoinductive and osteoconductive properties conducive for bone fusion. By using a patient's own bone, there is less chance of rejection, infection, and significant cost by not having to rely on bone substitute.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A collector used to collect cut bone, comprising:
   (a) a container body generally cylindrical in shape, defining an interior containment space for receiving and retaining collected bone, and having an open end providing access to the interior containment space for removal of collected bone from the interior containment space; and
   (b) a cap removably attached to the container body in covering relation to the open end of the container body;
   (c) wherein the cap comprises a sidewall having an intake opening for receiving therethrough a distal end of a rongeur into an interior receiving space of the cap for collecting cut bone from a cutting area thereof, and wherein the cap comprises a scraper attached to an underside of a top portion of the cap and extending downwardly therefrom within the interior receiving space of the cap in a direction toward the interior containment space for engaging and dislodging cut bone from the cutting area of the distal end of the rongeur when received through the intake opening when the cap is removably attached to the container body; and
   (d) wherein no scraper is located within the interior containment space of the container body when the cap is removably attached to the container body.

2. The collector of claim 1, wherein the scraper comprises a plurality of bristles attached to the underside of the top portion of the cap and extending downwardly therefrom in the direction toward the interior containment space when the cap is removably attached to the container body.

3. The collector of claim 1, wherein the cap comprises a stop by which the extent to which the distal end of the rongeur received through the intake opening is limited.

4. The collector of claim 1, wherein the scraper comprises a brush attached to the underside of the top portion of the cap and extending downwardly therefrom in the direction toward the interior containment space when the cap is removably attached to the container body.

5. The collector of claim 3, wherein the stop comprises a wall of the cap.

6. A collector comprising a container defining a first interior space and a removable cap attached to the container, the cap defining a second interior space separate from the first interior space and comprising a sidewall and a top portion, with the sidewall defining an opening dimensioned for receiving a tip of a rongeur therethrough, and further comprising a scraper attached to an underside of the top portion of the cap and extending within the second interior space defined by the cap such that extension of the rongeur through the opening into the second interior space defined by the cap dislodges material carried in a cutting area of the rongeur, which dislodged material falls into and is received within the first interior space defined by the container, wherein the opening defined by the sidewall of the cap is the only opening from an exterior of the collector to the first interior space defined by the container when the removable cap is attached to the container.

7. The collector of claim 1, wherein the cap comprises a screw-on cap that is removably attached by threaded engagement with the container body in covering relation to the open end of the container body.

8. The collector of claim 1, wherein the container body comprises a sidewall at least a portion of which is transparent for viewing of cut bone collected within the containment space.

9. A collector used to collect cut bone, comprising:
   (a) a container body defining an interior containment space for receiving and retaining collected bone, and having an open end for access to the interior containment space; and
   (b) a cap removably attached to the container body in covering relation to the open end of the container body;
   (c) wherein the cap comprises a sidewall defining an intake opening for receiving therethrough a distal end of a rongeur;
   (d) wherein the cap defines a second interior space separate from the interior containment space defined by the container body;

(e) wherein the cap comprises a scraper extending within the second interior space for engaging and dislodging cut bone from the cutting area of the distal end of the rongeur received through the intake opening when the cap is removably attached to the container body, whereby cut bone dislodged from the rongeur within the second interior space defined by the cap is received within the interior containment space defined by the container body; and (f) wherein the interior containment space defined by the container body is devoid of any scraper for unobstructed receipt of cut bone dislodged from the rongeur within the second interior space defined by the cap.

10. The collector of claim 9, wherein the container body is generally cylindrical in shape.

11. The collector of claim 9, wherein the cap comprises a screw-on cap that is removably attached in threaded engagement with the container body.

12. The collector of claim 9, wherein the container body comprises a sidewall at least a portion of which is transparent for viewing of cut bone within the interior containment space.

13. The collector of claim 9, wherein the scraper is attached to an underside of the cap and extends downwardly therefrom in a direction toward the interior containment space of the container body when the cap is removably attached to the open end of the container body.

14. The collector of claim 9, wherein a top portion of the cap also defines the intake opening.

15. The collector of claim 9, comprising additional scrapers extending within the second interior space for engaging and dislodging cut bone from the cutting area of the distal end of the rongeur received through the intake opening when the cap is removably attached to the container body.

16. The collector of claim 6, wherein the cap comprises a screw-on cap that is removably attached by threaded engagement with the container in covering relation to an open end of the container.

17. The collector of claim 1, wherein the open end of the container body provides the only access of the container body from an exterior of the collector to the interior containment space for removal of collected bone from the interior containment space.

18. The collector of claim 1, wherein the intake opening provides the only access of the cap from an exterior of the collector to the interior receiving space when the cap is removably attached to the container body.

* * * * *